(12) United States Patent
Nicolaides et al.

(10) Patent No.: US 6,737,268 B1
(45) Date of Patent: May 18, 2004

(54) METHOD FOR GENERATING GENETICALLY ALTERED ANTIGENS

(75) Inventors: Nicholas C. Nicolaides, Boothwyn, PA (US); Luigi Grasso, Philadelphia, PA (US); Philip M. Sass, Audubon, PA (US)

(73) Assignee: Morphotek, Inc., Exton, PA (US)

(*) Notice: Subject to any disclaimer, the term of this patent is extended or adjusted under 35 U.S.C. 154(b) by 0 days.

(21) Appl. No.: 09/712,691

(22) Filed: Nov. 14, 2000

(51) Int. Cl.$^7$ .......................... C12N 15/00; C12N 15/63

(52) U.S. Cl. .................. 435/325; 435/320.1; 435/69.1; 435/455

(58) Field of Search .................. 800/2, 14; 514/96; 424/93.2; 435/320.1, 455, 325, 69.1; 536/23.1

(56) References Cited

U.S. PATENT DOCUMENTS

| | | | |
|---|---|---|---|
| 5,885,827 | A | 3/1999 | Wabl et al. ............ 435/320.1 |
| 5,907,079 | A | 5/1999 | Mak et al. |
| 6,146,894 | A | 11/2000 | Nicolaides et al. |
| 6,191,268 | B1 | 2/2001 | Liskay et al. |
| 6,287,862 | B1 | 9/2001 | delCardayre et al. |
| 2002/0055106 | A1 * | 5/2002 | Nicolaides et al. ............ 435/6 |
| 2002/0068284 | A1 * | 6/2002 | Nicoladies et al. ............ 435/6 |
| 2002/0128460 | A1 * | 9/2002 | Nicolaides et al. ............ 536/23 |

FOREIGN PATENT DOCUMENTS

| | | |
|---|---|---|
| CA | 2 240 609 | 10/1999 |
| WO | WO 97/05268 | 2/1997 |
| WO | WO 97/08312 | 3/1997 |
| WO | 99/19492 | 4/1999 |

OTHER PUBLICATIONS

Verma et al. Gene therapy promises, problems and prospects pp. 239–242 vol. 389 1997.*
Russell et al. Structural features can be unconserved in proteins with similar folds pp. 332–350 1994.*
Ngo et al. Computational complexity, protein structure prediction, and the levinthal paradox pp. 491–495 1994.*
Rulicke et al. Special review series–gene manipulation and integrative physiology pp. 589–600 1996.*
Bishop Chromosomal insertion of foreign DNA pp. 607–619 1996.*
Polejaeva et al. New advances in somatic cell nuclear transfer application in transgenesis pp. 117–126 2000.*
Anderson Human gene therapy pp. 25–30 1998.*
Bork, 2000, Genome Research 10:398–400.*
Brenner, 1999, Trends in Genetics 15: 132.*
Bork et al., 1996, Trends in Genetics 12:425–427.*
Aronshtam, A., et al. "Dominant negative mutator mutations in the mutl gene of *Escherichia coli*", *Nucleic Acids Research*, 1996, 24(13), pp 2498–2504.
Cascalho M, et al. "Mismatch repair co–opted by hypermutation", *Science*, 1998, 279(20), pp 1207–1210.

Polaczek, P., et al. "Functional genetic tests of DNA mismatch repair protein activity in *Saccharomyces cerevisiae*", *Gene*, 1998, 213(1–2), pp 159–167.
Culligan, K.M., et al., "DNA mismatch repair in plants," *Plant Physiol.*, 1997, 15, XP–002099372, 833–839.
Jean, M., et al., "Isolation and characterization of AtMLH1, a MutL homologue from *Arabidopsis thaliana*," *Mol. Gen. Genet.*, 1999, 262, XP–000986138, 633–642.
Lipkin, S.M., et al., "MLH3: a DNA mismatch repair gene associated with mammalian microsatellite instability," *Nature Genetics*, 2000, 24, XP–002165243, 27–35.
Kong, Q., "PMS2–deficiency diminishes hypermutation of a $\lambda_1$ transgene in young but not older mice," *Molecular Immunology 36*, 1999, 83–91.
Schrader, C.E., et al., "Reduced isotype switching in splenic B cells from mice deficient in mismatch repair enzymes," *J. Exp. Med.*, 1999, 323–330.
Vora, K.A., et al., "Severe attenuation of the B celll immune response in Msh2–deficient mice," *J. Exp. Med.*, 1999, 189(3), 471–481.
Winter, D.B., et al., "Altered spectra of hypermutation in antibodies from mice deficient for the DNA mismatch repair protein PMS2," *Proc. Natl. Acad. Sci. USA*, 1998, 95, 6953–6958.
Fishel, R., et al., "the human mutator gene homolog MSH2 and its association with hereditary nonpolyposis colon cancer," *Cell*, 1993, 7, 1027–1038.
Hamilton, S.R., et al., "The molecular basis of turcot's syndrome," *N. Eng. J. Med.*, 1995, 332(13). 839–847.
Nicolaides, N.C., et al., "Molecular cloning of the N–Terminus of GTBP," *Genomics*, 1996, 31, 395–397.
Parsons, R., et al., "Mismatch repair deficiency in phenotypically normal human cells," *Science*, 1995, 268, 738–740.
Chakravarti, D. et al., "Relating aromatic hydrocarbon–induced DNA adducts and c–H–ras mutations in mouse skin papillomas: The role of apurinic sites", *Proc. Natl. Acad. Sci. USA*, Oct. 1995, vol. 92, pp. 10422–10426.
Quian, Y. et al., "Molecular events after antisense inhibition of hMSH2 in a HeLa cell line", *Mutation Research*, Oct. 12, 1998, vol. 418, pp. 61–71.
Yu, Y. et al., "Adriamycin induces large deletions as a major type of mutation in CHO cells", *Mutation Research*, Nov. 1994, vol. 325, pp. 91–98.

(List continued on next page.)

*Primary Examiner*—Dave T. Nguyen
(74) *Attorney, Agent, or Firm*—Woodcock Washburn LLP

(57) ABSTRACT

Dominant negative alleles of human mismatch repair genes can be used to generate hypermutable cells and organisms. By introducing these genes into cells and transgenic animals, new cell lines and animal varieties with novel and useful properties can be prepared more efficiently than by relying on the natural rate of mutation. These methods are useful for generating genetic diversity within genes encoding for therapeutic antigens to produce altered polypeptides with enhanced antigenic and immunogenic activity. Moreover, these methods are useful for generating effective vaccines.

10 Claims, 4 Drawing Sheets-

OTHER PUBLICATIONS

Liu et al., "Analysis of Mismatch Repair Genes in Hereditary Non–polyposis Colorectal Cancer Patients", *Nature Medicine*, Feb. 1996, 2(2), 169–174.

Ma et al., "Dominant Negative Experssion of hPMS2 Creates Isogenic Mismatch Repair Deficient Human Colon Cancer Cell Lines", *Proc. Am. Assoc. Cancer Res.*, Mar. 1998, 39, p. 460 (Abstract #3130).

Allen, D., et al., "MutS mediates heteroduplex loop formation by a translocation mechanism," *EMBO J.*, 1997, 16(14), 4467–4476.

Anders, R.F., "Part iv: Vaccines against asexual blood stages of plasmodium falciparum," *New Generation Vaccines*, 2$^{nd}$ Ed., Revised and Expanded, 1997, 1035–1055.

Ausiello, C.M., et al., "Cell–mediated immune responses in four–year–old children after primary immunization with acellular pertussis vaccines," *Infection and Immunity*, 1999, 67(8), 4064–4071.

Baker, S.M., et al., "Male mice defective in the DNA mismatch repair gene PMS2 exhibit abnormal chromosome synapsis in meiosis," *Cell*, 1995, 82, 309–319.

Bell, C.J., et al., "Assignment of 30 microsatellite loci to the linkage map of *arabidopsis,*" *Enomics*, 1994, 19, 137–144.

Bjornson, K., et al., "Modulation of MutS ATP hydrolysis by DNA cofactors," *Biochemistry*, 2000, 39, 3176–3183.

Boyce, T.G., et al., "Safety and immunogenicity of adjuvanted and unadjuvanted subunit influenza vaccines administered intranasally to healthy adults," *Vaccine*, 2001, 19, 217–226.

Bronner C.E., et al., "Mutation in the DNA mismatch repair gene homologue hMLH1 is associated with hereditary non–polyposis colon cancer," *Nature*, 1994, 368, 258–261.

Brostoff, S., "The development and use of T cell receptor peptide vaccines," *Immun. Of Proteins and Peptides VIII*, 1995, 249–254.

Corbel, M.J., "Reasons for instability of bacterial vaccines," *Dev. Biol. Stand.*, 1996, 87, 113–124.

Devos, R., et al., Molecular cloning of human interleukin 2cDNA and its expression in *E. coli, Nucleic Acids Research*, 1983, 11(13), 4307–4323.

de Wind, N., et al., "Inactivation of the mouse Msh2 gene results in mismatch repair deficiency, methylation tolerance, hyperrecombination, and predisposition to cancer," *Cell*, 1995, 82, 321–330.

Drummond, J.T., et al., "Isolation of an hMSH2–p160 heterodimer that restores DNA mismatch repair to tumor cells," *Science*, 1995, 268, 1909–1912.

Drummond, J.T., et al., "Cisplatin and adriamycin resistance are associated with mutlα and mismatch repair deficiency in an ovarian tumor cell line," *J. Biological Chemistry*, 1996, 271(33), 19645–19648.

Edelmann, W., et al., "Meiotic pachytene arrest in MLH1 – deficient mice," *Cell*, 1996, 85, 1125–1134.

Eshleman, J.R., et al., "Mismatch repair defects in human carcinogenesis," *Human Molecular Genetics*, 1996, 5, 1489–1494.

Galio, L., et al., "ATP hydrolysis–dependent formation of a dynamic ternary nucleoprotein complex with MutS and MutL," *Nucleic Acids Research*, 1999, 27(11), 2325–2331.

Grasso, L., "Molecular analysis of human interleukin–9 receptor transcripts in peripheral blood mononuclear cells," *J. Biological Chemistry*, 1998, 273(37), 24016–24024.

Harfe, B.D., "DNA mismatch repair and genetic instability," *Annu. Rev. Genet.*, 2000, 34, 359–399.

Hoang, J., et al., "BAT–26, an indicator of the replication error phenotype in colorectal cancers and cell lines," *Cancer Research*, 1997, 57, 300–303.

Honma, M., et al., "Cytotoxic and mutagenic responses to X–rays and chemical mutagens in normal and p53–mutated human lymphoblastoid cells," *Mutation Research*, 1997, 374, 89–98.

John, T.M., "The final stages of the global eradication of polio," *New England Journal of Medicine*, 2000, 806–807.

Jiricny, J., et al., "Mismatch repair defects in cancer," *Curr. Opin. Genet. Dev.*, 2000, 10, 157–161.

Karran, P., et al., "Genomic instability and tolerance to alkylating agents," *Cancer Surveys*, 1996, 28, 69–71.

Kim, K., et al., "Conformationally appropriate expression of the toxoplasma antigen SAG1 (p30) in CHO cells," *Infection and Immunity*, 1994, 62(1), 203–209.

Kniskern, P.J., et al., "Characterization and evaluation of a recombinant hepatitis B vaccine expressed in yeast defective for N–linked hyperglycosylation," *Vaccine*, 1994, 12(11), 1021–1025.

Leach, F.S., et al., "Mutations of a mutS homolog in hereditary nonpolyposis colorectal cancer," *Cell*, 1993, 75, 1215–1225.

Lechmann, M., et al., "Vaccine development for hepatitis C," *Seminars in Liver Disease*, 2000, 20(2), 211–226.

Liu, T., et al., "Microsatellite instability as a predictor of a mutation in a DNA mismatch repair gene in familial colorectal cancer," *Genes, Chromosomes & Cancer*, 2000, 27, 17–25.

McCallum, C.M., "Targeted screening for induced mutations," *Nature Biotechnology*, 2000, 18, 455–457.

McLeod, R., et al., "Immunogenetics in the analysis of resistance to intracellular pathogens," *Current Opinion in Immunology*, ISSN 0952–7915, 1995, 7, 539–552.

Modrich, P., "Mismatch repair, genetic stability, and cancer," *Science*, 1994, 266, 1959–1960.

Neuberger, M., et al., "Mice perform a human repertoire," *Nature*, 1997, 386, 25–26.

Nicolaides, N.C., et al., "Analysis of the 5' region of PMS2 reveals heterogeneous transcripts and a novel overlapping gene," *Genomics*, 1995, 29, 329–334.

Nicolaides, N.C., et al., "Genomic organization of the human PMS2 gene family," *Genomics*, 1995, 30, 195–206.

Nicolaides, N.C., "A naturally occurring hPMS2 mutation can confer a dominant negative nutator phenotype," *Mol. Cell. Biol.*, 1998, 18(3), 1635–1641.

Nicolaides, N.C., et al., "The jun family members, c–jun and junD, transactivate the human c–myb, promotor via an Ap1–like element," *J. Biological Chemistry*, 1992, 267(27), 19655–19672.

Nicolaides, N.C., et al., "Positive autoregulation of c–myb, expression via Myb binding sites in the 5' flanking region of the human c–myb gene," *Moecular and Cellular Biology*, 1991, 11(12), 6166–6176.

Nicolaides, N.C., et al., "Mutations of two PMS homologues in hereditary nonpolyposis colon cancer," *Nature*, 1994, 371, 75–80.

Nicolaides, N.C., et al., "Interleukin 9: A candidate gene for asthma," *Proc. Nat. Acad. Sci. USA*, 1997, 94, 13175–13180.

Orenstein, W.A., et al., "Measles eradication: Is it in our future," *Am. J. Public Health*, 2000, 90(10), 1521–1524.

Palombo, F., et al., "Mismatch repair and cancer," *Nature*, 1994, 367, 417.

Papadopoulos, N., et al., "Mutation of a mutL homolog in hereditary colon cancer,"*Science*, 1994, 263, 1625–1629.

Papadopoulos, N., et al., "Mutations of GTBP in genetically unstable cells," *Science*, 1995, 268, 1915–1917.

Parsons, R., et al., "hypermutability and mismatch repair deficiency in RER+ tumor cells," *Cell*, 1993, 75, 1227–1236.

Peinado, M.A., et al., "Isolation and characterization of allelic lossesand gains in colorectal tumors by arbitrarily primed polymerase chain reaction," *Proc. Natl. Acad. Sci. USA*, 1992, 89, 10065–10069.

Perucho, M., et al., "Cancer of the microsatelite mutator phenotype," *Biol. Chem.*, 1996, 377, 675–684.

Prolla, T.A., et al., "MLH1, PMS1, and MSH2 interactions during the initiation of DNA mismatch repair in yeast," *Science*, 1994, 265, 1091–1093.

Sela, M., "Structural components responsible for peptide antigenicity," *Applied Biochemistry and Biotechnology*, 2000, 83, Catalytic and Superantibodies, 63–70.

Spampinato, C., et al., "The MutL ATPase is required for mismatch repair," *J. Biological Chemistry*, 2000, 275(13), 9863–9869.

Strand, M., et al., "Destabilization of tracts of simple repetitive DNA in yeast by mutations affecting DNA mismatch repair," *Nature*, 1993, 365, 274–276.

Su, S., et al., "Dispair specificity of methyl–directed DNA mismatch correction In Vitro," *J. Biological Chemistry*, 1988, 263(14), 6829–6835.

Wheeler, J.M.D.,et al., "The role of hypermethylation of the hMLH1 promoter region in HNPCC verus MSI+sporadic colorectal cancers," *J. Med. Genet.*, 2000, 588–592.

* cited by examiner

Figure 1
| Panel A: TKvect/pCAR-OF cells | Panel B: TKPMS134/pCAR-OF cells |
|---|---|
| 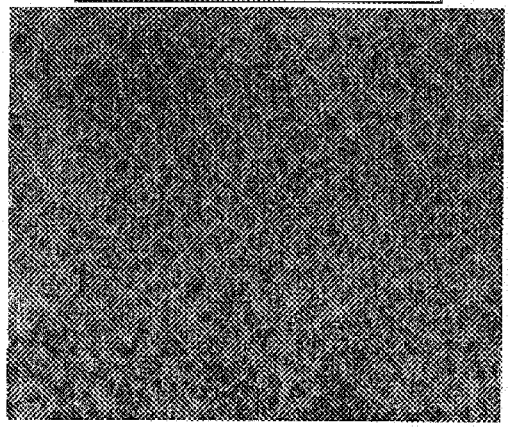 | 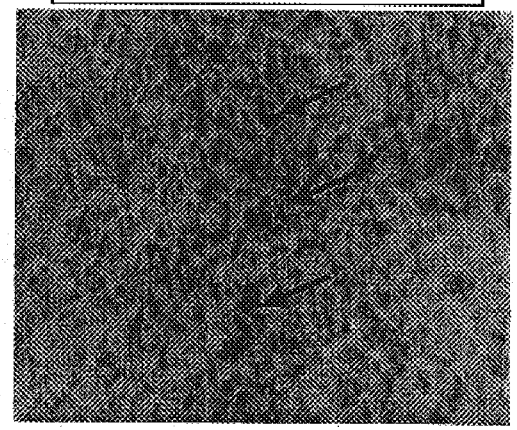 |

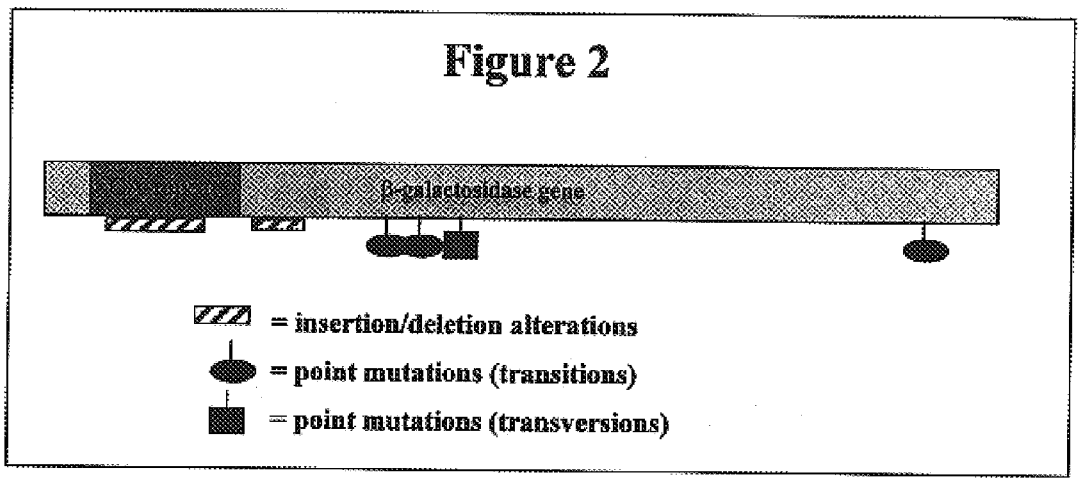

*Aagctt*ccatgtacaggatgcaactcctgtcttgcattgcactaagtcttgcacttgtcacaaacagtgcaCAAAAGCT
GGAGCTCCACCGCGGTGGCGGCCGCTCTAGAACTAGTGGATCCCCC
GGGGCTGCAGGAATTCGATATCAAGCcaccatcaccatcaccactagtag*aagctt*-3'

SEQUENCE LISTING

```
<160> NUMBER OF SEQ ID NOS: 17

<210> SEQ ID NO 1
<211> LENGTH: 86
<212> TYPE: DNA
<213> ORGANISM: Artificial Sequence
<220> FEATURE:
<223> OTHER INFORMATION: Description of Artificial Sequence:sense primer

<400> SEQUENCE: 1
aagcttccat gtacaggatg caactcctgt cttgcattgc actaagtctt gcacttgtca        60
caaacagtgc acaaaagctg gagctc                                             86

<210> SEQ ID NO 2
<211> LENGTH: 51
<212> TYPE: DNA
<213> ORGANISM: Artificial Sequence
<220> FEATURE:
<223> OTHER INFORMATION: Description of Artificial Sequence:antisense
      primer

<400> SEQUENCE: 2
ccggatccct actagtggtg atggtgatgg tggcttgata tcgaattcct g                 51

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence:sense primer

<400> SEQUENCE: 3
catgtacagg atgcaactcc tg                                                 22
```

```
<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence:antisense
      primer

<400> SEQUENCE: 4
tactagtggt gatggtgatg gtg                                            23

<210> SEQ ID NO 5
<211> LENGTH: 859
<212> TYPE: PRT
<213> ORGANISM: Mus musculus

<400> SEQUENCE: 5
```

| Met | Glu | Gln | Thr | Glu | Gly | Val | Ser | Thr | Glu | Cys | Ala | Lys | Ala | Ile | Lys |
|-----|-----|-----|-----|-----|-----|-----|-----|-----|-----|-----|-----|-----|-----|-----|-----|
| 1 | | | | 5 | | | | | 10 | | | | | 15 | |

| Pro | Ile | Asp | Gly | Lys | Ser | Val | His | Gln | Ile | Cys | Ser | Gly | Gln | Val | Ile |
| | | | 20 | | | | | 25 | | | | | 30 | | |

| Leu | Ser | Leu | Ser | Thr | Ala | Val | Lys | Glu | Leu | Ile | Glu | Asn | Ser | Val | Asp |
| | | 35 | | | | | 40 | | | | | 45 | | | |

| Ala | Gly | Ala | Thr | Thr | Ile | Asp | Leu | Arg | Leu | Lys | Asp | Tyr | Gly | Val | Asp |
| | 50 | | | | | 55 | | | | | 60 | | | | |

| Leu | Ile | Glu | Val | Ser | Asp | Asn | Gly | Cys | Gly | Val | Glu | Glu | Asn | Phe |
| 65 | | | | | 70 | | | | | 75 | | | | | 80 |

| Glu | Gly | Leu | Ala | Leu | Lys | His | His | Thr | Ser | Lys | Ile | Gln | Glu | Phe | Ala |
| | | | | 85 | | | | | 90 | | | | | 95 | |

| Asp | Leu | Thr | Gln | Val | Glu | Thr | Phe | Gly | Phe | Arg | Gly | Glu | Ala | Leu | Ser |
| | | | 100 | | | | | 105 | | | | | 110 | | |

| Ser | Leu | Cys | Ala | Leu | Ser | Asp | Val | Thr | Ile | Ser | Thr | Cys | His | Gly | Ser |
| | | 115 | | | | | 120 | | | | | 125 | | | |

| Ala | Ser | Val | Gly | Thr | Arg | Leu | Val | Phe | Asp | His | Asn | Gly | Lys | Ile | Thr |
| | 130 | | | | | 135 | | | | | 140 | | | | |

| Gln | Lys | Thr | Pro | Tyr | Pro | Arg | Pro | Lys | Gly | Thr | Thr | Val | Ser | Val | Gln |
| 145 | | | | | 150 | | | | | 155 | | | | | 160 |

| His | Leu | Phe | Tyr | Thr | Leu | Pro | Val | Arg | Tyr | Lys | Glu | Phe | Gln | Arg | Asn |
| | | | | 165 | | | | | 170 | | | | | 175 | |

| Ile | Lys | Lys | Glu | Tyr | Ser | Lys | Met | Val | Gln | Val | Leu | Gln | Ala | Tyr | Cys |
| | | | 180 | | | | | 185 | | | | | 190 | | |

| Ile | Ile | Ser | Ala | Gly | Val | Arg | Val | Ser | Cys | Thr | Asn | Gln | Leu | Gly | Gln |
| | | 195 | | | | | 200 | | | | | 205 | | | |

| Gly | Lys | Arg | His | Ala | Val | Val | Cys | Thr | Ser | Gly | Thr | Ser | Gly | Met | Lys |
| | 210 | | | | | 215 | | | | | 220 | | | | |

| Glu | Asn | Ile | Gly | Ser | Val | Phe | Gly | Gln | Lys | Gln | Leu | Gln | Ser | Leu | Ile |
| 225 | | | | | 230 | | | | | 235 | | | | | 240 |

| Pro | Phe | Val | Gln | Leu | Pro | Pro | Ser | Asp | Ala | Val | Cys | Glu | Glu | Tyr | Gly |
| | | | | 245 | | | | | 250 | | | | | 255 | |

| Leu | Ser | Thr | Ser | Gly | Arg | His | Lys | Thr | Phe | Ser | Thr | Phe | Arg | Ala | Ser |
| | | | 260 | | | | | 265 | | | | | 270 | | |

| Phe | His | Ser | Ala | Arg | Thr | Ala | Pro | Gly | Gly | Val | Gln | Gln | Thr | Gly | Ser |
| | | 275 | | | | | 280 | | | | | 285 | | | |

| Phe | Ser | Ser | Ser | Ile | Arg | Gly | Pro | Val | Thr | Gln | Gln | Arg | Ser | Leu | Ser |
| | 290 | | | | | 295 | | | | | 300 | | | | |

| Leu | Ser | Met | Arg | Phe | Tyr | His | Met | Tyr | Asn | Arg | His | Gln | Tyr | Pro | Phe |
| 305 | | | | | 310 | | | | | 315 | | | | | 320 |

```
Val Val Leu Asn Val Ser Val Asp Ser Glu Cys Val Asp Ile Asn Val
            325                 330                 335

Thr Pro Asp Lys Arg Gln Ile Leu Leu Gln Glu Lys Leu Leu Leu
            340                 345                 350

Ala Val Leu Lys Thr Ser Leu Ile Gly Met Phe Asp Ser Asp Ala Asn
            355                 360                 365

Lys Leu Asn Val Asn Gln Gln Pro Leu Leu Asp Val Glu Gly Asn Leu
            370                 375                 380

Val Lys Leu His Thr Ala Glu Leu Glu Lys Pro Val Pro Gly Lys Gln
385                 390                 395                 400

Asp Asn Ser Pro Ser Leu Lys Ser Thr Ala Asp Glu Lys Arg Val Ala
            405                 410                 415

Ser Ile Ser Arg Leu Arg Glu Ala Phe Ser Leu His Pro Thr Lys Glu
            420                 425                 430

Ile Lys Ser Arg Gly Pro Glu Thr Ala Glu Leu Thr Arg Ser Phe Pro
            435                 440                 445

Ser Glu Lys Arg Gly Val Leu Ser Ser Tyr Pro Ser Asp Val Ile Ser
            450                 455                 460

Tyr Arg Gly Leu Arg Gly Ser Gln Asp Lys Leu Val Ser Pro Thr Asp
465                 470                 475                 480

Ser Pro Gly Asp Cys Met Asp Arg Glu Lys Ile Glu Lys Asp Ser Gly
            485                 490                 495

Leu Ser Ser Thr Ser Ala Gly Ser Glu Glu Phe Ser Thr Pro Glu
            500                 505                 510

Val Ala Ser Ser Phe Ser Ser Asp Tyr Asn Val Ser Ser Leu Glu Asp
            515                 520                 525

Arg Pro Ser Gln Glu Thr Ile Asn Cys Gly Asp Leu Asp Cys Arg Pro
530                 535                 540

Pro Gly Thr Gly Gln Ser Leu Lys Pro Glu Asp His Gly Tyr Gln Cys
545                 550                 555                 560

Lys Ala Leu Pro Leu Ala Arg Leu Ser Pro Thr Asn Ala Lys Arg Phe
            565                 570                 575

Lys Thr Glu Glu Arg Pro Ser Asn Val Asn Ile Ser Gln Arg Leu Pro
            580                 585                 590

Gly Pro Gln Ser Thr Ser Ala Ala Glu Val Asp Val Ala Ile Lys Met
            595                 600                 605

Asn Lys Arg Ile Val Leu Leu Glu Phe Ser Leu Ser Ser Leu Ala Lys
            610                 615                 620

Arg Met Lys Gln Leu Gln His Leu Lys Ala Gln Asn Lys His Glu Leu
625                 630                 635                 640

Ser Tyr Arg Lys Phe Arg Ala Lys Ile Cys Pro Gly Glu Asn Gln Ala
            645                 650                 655

Ala Glu Asp Glu Leu Arg Lys Glu Ile Ser Lys Ser Met Phe Ala Glu
            660                 665                 670

Met Glu Ile Leu Gly Gln Phe Asn Leu Gly Phe Ile Val Thr Lys Leu
            675                 680                 685

Lys Glu Asp Leu Phe Leu Val Asp Gln His Ala Ala Asp Glu Lys Tyr
            690                 695                 700

Asn Phe Glu Met Leu Gln Gln His Thr Val Leu Gln Ala Gln Arg Leu
705                 710                 715                 720

Ile Thr Pro Gln Thr Leu Asn Leu Thr Ala Val Asn Glu Ala Val Leu
            725                 730                 735
```

```
Ile Glu Asn Leu Glu Ile Phe Arg Lys Asn Gly Phe Asp Phe Val Ile
            740                 745                 750
Asp Glu Asp Ala Pro Val Thr Glu Arg Ala Lys Leu Ile Ser Leu Pro
        755                 760                 765
Thr Ser Lys Asn Trp Thr Phe Gly Pro Gln Asp Ile Asp Glu Leu Ile
    770                 775                 780
Phe Met Leu Ser Asp Ser Pro Gly Val Met Cys Arg Pro Ser Arg Val
785                 790                 795                 800
Arg Gln Met Phe Ala Ser Arg Ala Cys Arg Lys Ser Val Met Ile Gly
                805                 810                 815
Thr Ala Leu Asn Ala Ser Glu Met Lys Lys Leu Ile Thr His Met Gly
            820                 825                 830
Glu Met Asp His Pro Trp Asn Cys Pro His Gly Arg Pro Thr Met Arg
        835                 840                 845
His Val Ala Asn Leu Asp Val Ile Ser Gln Asn
    850                 855
```

<210> SEQ ID NO 6
<211> LENGTH: 3056
<212> TYPE: DNA
<213> ORGANISM: Mus musculus

<400> SEQUENCE: 6

```
gaattccggt gaaggtcctg aagaatttcc agattcctga gtatcattgg aggagacaga      60
taacctgtcg tcaggtaacg atggtgtata tgcaacagaa atgggtgttc ctggagacgc     120
gtcttttccc gagagcggca ccgcaactct cccgcggtga ctgtgactgg aggagtcctg     180
catccatgga gcaaaccgaa ggcgtgagta cagaatgtgc taaggccatc aagcctattg     240
atgggaagtc agtccatcaa atttgttctg ggcaggtgat actcagttta agcaccgctg     300
tgaaggagtt gatagaaaat agtgtagatg ctggtgctac tactattgat ctaaggctta     360
aagactatgg ggtggacctc attgaagttt cagacaatgg atgtggggta agaagaaaa     420
actttgaagg tctagctctg aaacatcaca catctaagat tcaagagttt gccgacctca     480
cgcaggttga aactttcggc tttcggggg aagctctgag ctctctgtgt gcactaagtg     540
atgtcactat atctacctgc cacgggtctg caagcgttgg gactcgactg gtgtttgacc     600
ataatgggaa aatcacccag aaaactccct accccgacc taaaggaacc acagtcagtg     660
tgcagcactt atttttataca ctacccgtgc gttacaaaga gtttcagagg aacattaaaa     720
aggagtattc caaaatggtg caggtcttac aggcgtactg tatcatctca gcaggcgtcc     780
gtgtaagctg cactaatcag ctcggacagg ggaagcggca cgctgtggtg tgcacaagcg     840
gcacgtctgg catgaaggaa aatatcgggt ctgtgtttgg ccagaagcag ttgcaaagcc     900
tcattccttt tgttcagctg cccctagtac acgctgtgtg tgaagagtac ggcctgagca     960
cttcaggacg ccacaaaacc ttttctacgt ttcgggcttc atttcacagt gcacgcacgg    1020
cgccgggagg agtgcaacag acaggcagtt tttcttcatc aatcagaggc cctgtgaccc    1080
agcaaaggtc tctaagcttg tcaatgaggt tttatcacat gtataaccgg catcagtacc    1140
catttgtcgt ccttaacgtt tccgttgact cagaatgtgt ggatattaat gtaactccag    1200
ataaaaggca aattctacta caagaagaga agctattgct ggccgtttta aagacctcct    1260
tgataggaat gtttgacagt gatgcaaaca agcttaatgt caaccagcag ccactgctag    1320
atgttgaagg taacttagta aagctgcata ctgcagaact agaaaagcct gtgccaggaa    1380
agcaagataa ctctccttca ctgaagagca cagcagacga gaaagggta gcatccatct    1440
```

```
ccaggctgag agaggccttt tctcttcatc ctactaaaga gatcaagtct aggggtccag   1500
agactgctga actgacacgg agttttccaa gtgagaaaag gggcgtgtta tcctcttatc   1560
cttcagacgt catctcttac agaggcctcc gtggctcgca ggacaaattg gtgagtccca   1620
cggacagccc tggtgactgt atggacagag agaaaataga aaagactcag ggctcagca   1680 gcacctcagc tggctctgag gaagagttca gcacccccaga agtggccagt agctttagca   1740
gtgactataa cgtgagctcc ctagaagaca gaccttctca ggaaaccata aactgtggtg   1800
acctggactg ccgtcctcca ggtacaggac agtccttgaa gccagaagac catggatatc   1860
aatgcaaagc tctacctcta gctcgtctgt cacccacaaa tgccaagcgc ttcaagacag   1920
aggaaagacc ctcaaatgtc aacatttctc aaagattgcc tggtcctcag agcacctcag   1980
cagctgaggt cgatgtagcc ataaaaatga ataagagaat cgtgctcctc gagttctctc   2040
tgagttctct agctaagcga atgaagcagt tacagcacct aaaggcgcag aacaaacatg   2100
aactgagtta cagaaaattt agggccaaga tttgccctgg agaaaaccaa gcagcagaag   2160
atgaactcag aaaagagatt agtaaatcga tgtttgcaga gatggagatc ttgggtcagt   2220
ttaacctggg atttatagta accaaactga agaggaccct cttcctggtg gaccagcatg   2280
ctgcggatga gaagtacaac tttgagatgc tgcagcagca cacggtgctc caggcgcaga   2340
ggctcatcac accccagact ctgaacttaa ctgctgtcaa tgaagctgta ctgatagaaa   2400
atctggaaat attcagaaag aatggctttg actttgtcat tgatgaggat gctccagtca   2460
ctgaaagggc taaattgatt tccttaccaa ctagtaaaaa ctggaccttt ggaccccaag   2520
atatagatga actgatcttt atgttaagtg acagccctgg ggtcatgtgc cggccctcac   2580
gagtcagaca gatgtttgct tccagagcct gtcggaagtc agtgatgatt ggaacggcgc   2640
tcaatgcgag cgagatgaag aagctcatca cccacatggg tgagatggac caccctgga   2700 actgccccca cggcaggcca accatgaggc acgttgccaa tctggatgtc atctctcaga   2760
actgacacac cccttgtagc atagagttta ttacagattg ttcggtttgc aaagagaagg   2820
ttttaagtaa tctgattatc gttgtacaaa aattagcatg ctgctttaat gtactggatc   2880
catttaaaag cagtgttaag gcaggcatga tggagtgttc ctctagctca gctacttggg   2940
tgatccggtg ggagctcatg tgagcccagg actttgagac cactccgagc cacattcatg   3000
agactcaatt caaggacaaa aaaaaaaaga tatttttgaa gcctttttaaa aaaaaa      3056
```

<210> SEQ ID NO 7
<211> LENGTH: 862
<212> TYPE: PRT
<213> ORGANISM: Homo sapiens

<400> SEQUENCE: 7

```
Met Glu Arg Ala Glu Ser Ser Thr Glu Pro Ala Lys Ala Ile Lys
  1               5                  10                  15

Pro Ile Asp Arg Lys Ser Val His Gln Ile Cys Ser Gly Gln Val Val
                 20                  25                  30

Leu Ser Leu Ser Thr Ala Val Lys Glu Leu Val Glu Asn Ser Leu Asp
             35                  40                  45

Ala Gly Ala Thr Asn Ile Asp Leu Lys Leu Lys Asp Tyr Gly Val Asp
         50                  55                  60

Leu Ile Glu Val Ser Asp Asn Gly Cys Gly Val Glu Glu Glu Asn Phe
     65                  70                  75                  80

Glu Gly Leu Thr Leu Lys His His Thr Ser Lys Ile Gln Glu Phe Ala
```

-continued

```
                85                  90                  95
Asp Leu Thr Gln Val Glu Thr Phe Gly Phe Arg Gly Glu Ala Leu Ser
            100                 105                 110

Ser Leu Cys Ala Leu Ser Asp Val Thr Ile Ser Thr Cys His Ala Ser
            115                 120                 125

Ala Lys Val Gly Thr Arg Leu Met Phe Asp His Asn Gly Lys Ile Ile
        130                 135                 140

Gln Lys Thr Pro Tyr Pro Arg Pro Arg Gly Thr Thr Val Ser Val Gln
145                 150                 155                 160

Gln Leu Phe Ser Thr Leu Pro Val Arg His Lys Glu Phe Gln Arg Asn
                165                 170                 175

Ile Lys Lys Glu Tyr Ala Lys Met Val Gln Val Leu His Ala Tyr Cys
            180                 185                 190

Ile Ile Ser Ala Gly Ile Arg Val Ser Cys Thr Asn Gln Leu Gly Gln
        195                 200                 205

Gly Lys Arg Gln Pro Val Val Cys Thr Gly Gly Ser Pro Ser Ile Lys
210                 215                 220

Glu Asn Ile Gly Ser Val Phe Gly Gln Lys Gln Leu Gln Ser Leu Ile
225                 230                 235                 240

Pro Phe Val Gln Leu Pro Pro Ser Asp Ser Val Cys Glu Glu Tyr Gly
                245                 250                 255

Leu Ser Cys Ser Asp Ala Leu His Asn Leu Phe Tyr Ile Ser Gly Phe
            260                 265                 270

Ile Ser Gln Cys Thr His Gly Val Gly Arg Ser Ser Thr Asp Arg Gln
        275                 280                 285

Phe Phe Phe Ile Asn Arg Arg Pro Cys Asp Pro Ala Lys Val Cys Arg
        290                 295                 300

Leu Val Asn Glu Val Tyr His Met Tyr Asn Arg His Gln Tyr Pro Phe
305                 310                 315                 320

Val Val Leu Asn Ile Ser Val Asp Ser Glu Cys Val Asp Ile Asn Val
                325                 330                 335

Thr Pro Asp Lys Arg Gln Ile Leu Leu Gln Glu Glu Lys Leu Leu Leu
            340                 345                 350

Ala Val Leu Lys Thr Ser Leu Ile Gly Met Phe Asp Ser Asp Val Asn
        355                 360                 365

Lys Leu Asn Val Ser Gln Gln Pro Leu Leu Asp Val Glu Gly Asn Leu
        370                 375                 380

Ile Lys Met His Ala Ala Asp Leu Glu Lys Pro Met Val Glu Lys Gln
385                 390                 395                 400

Asp Gln Ser Pro Ser Leu Arg Thr Gly Glu Glu Lys Lys Asp Val Ser
                405                 410                 415

Ile Ser Arg Leu Arg Glu Ala Phe Ser Leu Arg His Thr Thr Glu Asn
            420                 425                 430

Lys Pro His Ser Pro Lys Thr Pro Glu Pro Arg Arg Ser Pro Leu Gly
        435                 440                 445

Gln Lys Arg Gly Met Leu Ser Ser Thr Ser Gly Ala Ile Ser Asp
        450                 455                 460

Lys Gly Val Leu Arg Pro Gln Lys Glu Ala Val Ser Ser Ser His Gly
465                 470                 475                 480

Pro Ser Asp Pro Thr Asp Arg Ala Glu Val Glu Lys Asp Ser Gly His
                485                 490                 495

Gly Ser Thr Ser Val Asp Ser Glu Gly Phe Ser Ile Pro Asp Thr Gly
            500                 505                 510
```

```
Ser His Cys Ser Ser Glu Tyr Ala Ala Ser Ser Pro Gly Asp Arg Gly
    515                 520                 525

Ser Gln Glu His Val Asp Ser Gln Glu Lys Ala Pro Glu Thr Asp Asp
    530                 535                 540

Ser Phe Ser Asp Val Asp Cys His Ser Asn Gln Glu Asp Thr Gly Cys
545                 550                 555                 560

Lys Phe Arg Val Leu Pro Gln Pro Thr Asn Leu Ala Thr Pro Asn Thr
                565                 570                 575

Lys Arg Phe Lys Lys Glu Glu Ile Leu Ser Ser Ser Asp Ile Cys Gln
            580                 585                 590

Lys Leu Val Asn Thr Gln Asp Met Ser Ala Ser Gln Val Asp Val Ala
        595                 600                 605

Val Lys Ile Asn Lys Lys Val Val Pro Leu Asp Phe Ser Met Ser Ser
610                 615                 620

Leu Ala Lys Arg Ile Lys Gln Leu His His Glu Ala Gln Gln Ser Glu
625                 630                 635                 640

Gly Glu Gln Asn Tyr Arg Lys Phe Arg Ala Lys Ile Cys Pro Gly Glu
                645                 650                 655

Asn Gln Ala Ala Glu Asp Glu Leu Arg Lys Glu Ile Ser Lys Thr Met
            660                 665                 670

Phe Ala Glu Met Glu Ile Ile Gly Gln Phe Asn Leu Gly Phe Ile Ile
        675                 680                 685

Thr Lys Leu Asn Glu Asp Ile Phe Ile Val Asp Gln His Ala Thr Asp
        690                 695                 700

Glu Lys Tyr Asn Phe Glu Met Leu Gln Gln His Thr Val Leu Gln Gly
705                 710                 715                 720

Gln Arg Leu Ile Ala Pro Gln Thr Leu Asn Leu Thr Ala Val Asn Glu
                725                 730                 735

Ala Val Leu Ile Glu Asn Leu Glu Ile Phe Arg Lys Asn Gly Phe Asp
            740                 745                 750

Phe Val Ile Asp Glu Asn Ala Pro Val Thr Glu Arg Ala Lys Leu Ile
        755                 760                 765

Ser Leu Pro Thr Ser Lys Asn Trp Thr Phe Gly Pro Gln Asp Val Asp
770                 775                 780

Glu Leu Ile Phe Met Leu Ser Asp Ser Pro Gly Val Met Cys Arg Pro
785                 790                 795                 800

Ser Arg Val Lys Gln Met Phe Ala Ser Arg Ala Cys Arg Lys Ser Val
                805                 810                 815

Met Ile Gly Thr Ala Leu Asn Thr Ser Glu Met Lys Lys Leu Ile Thr
            820                 825                 830

His Met Gly Glu Met Asp His Pro Trp Asn Cys Pro His Gly Arg Pro
        835                 840                 845

Thr Met Arg His Ile Ala Asn Leu Gly Val Ile Ser Gln Asn
        850                 855                 860

<210> SEQ ID NO 8
<211> LENGTH: 2771
<212> TYPE: DNA
<213> ORGANISM: Homo sapiens

<400> SEQUENCE: 8
cgaggcggat cgggtgttgc atccatggag cgagctgaga gctcgagtac agaacctgct    60
aaggccatca aacctattga tcggaagtca gtccatcaga tttgctctgg gcaggtggta   120
```

-continued

| | |
|---|---|
| ctgagtctaa gcactgcggt aaaggagtta gtagaaaaca gtctggatgc tggtgccact | 180 |
| aatattgatc taaagcttaa ggactatgga gtggatctta ttgaagtttc agacaatgga | 240 |
| tgtggggtag aagaagaaaa cttcgaaggc ttaactctga acatcacac atctaagatt | 300 |
| caagagtttg ccgacctaac tcaggttgaa acttttggct ttcgggggga agctctgagc | 360 |
| tcactttgtg cactgagcga tgtcaccatt tctacctgcc acgcatcggc gaaggttgga | 420 |
| actcgactga tgtttgatca caatgggaaa attatccaga aaccccccta ccccgcccc | 480 |
| agagggacca cagtcagcgt gcagcagtta ttttccacac tacctgtgcg ccataaggaa | 540 |
| tttcaaagga atattaagaa ggagtatgcc aaaatggtcc aggtcttaca tgcatactgt | 600 |
| atcatttcag caggcatccg tgtaagttgc accaatcagc ttggacaagg aaaacgacag | 660 |
| cctgtggtat gcacaggtgg aagccccagc ataaggaaa atatcggctc tgtgtttggg | 720 |
| cagaagcagt tgcaaagcct cattccttt gttcagctgc ccctagtga ctccgtgtgt | 780 |
| gaagagtacg gtttgagctg ttcggatgct ctgcataatc ttttttacat ctcaggtttc | 840 |
| atttcacaat gcacgcatgg agttggaagg agttcaacag acagacagtt tttctttatc | 900 |
| aaccggcggc cttgtgaccc agcaaaggtc tgcagactcg tgaatgaggt ctaccacatg | 960 |
| tataatcgac accagtatcc atttgttgtt cttaacattt ctgttgattc agaatgcgtt | 1020 |
| gatatcaatg ttactccaga taaaaggcaa attttgctac aagaggaaaa gcttttgttg | 1080 |
| gcagtttta agacctcttt gataggaatt tttgatagtg atgtcaacaa gctaaatgtc | 1140 |
| agtcagcagc cactgctgga tgttgaaggt aacttaataa aaatgcatgc agcggatttg | 1200 |
| gaaaagccca tggtagaaaa gcaggatcaa tccccttcat taaggactgg agaagaaaa | 1260 |
| aaagacgtgt ccatttccag actgcgagag gcctttctc ttcgtcacac aacagagaac | 1320 |
| aagcctcaca gcccaaagac tccagaacca agaaggagcc ctctaggaca gaaaagggt | 1380 |
| atgctgtctt ctagcacttc aggtgccatc tctgacaaag gcgtcctgag acctcagaaa | 1440 |
| gaggcagtga gttccagtca cggacccagt gaccctacgg acagagcgga ggtggagaag | 1500 |
| gactcggggc acggcagcac ttccgtggat tctgaggggt tcagcatccc agacacgggc | 1560 |
| agtcactgca gcagcgagta tgcggccagc tccccagggg acagggctc gcaggaacat | 1620 |
| gtggactctc aggagaaagc gcctgaaact gacgactctt tttcagatgt ggactgccat | 1680 |
| tcaaaccagg aagataccgg atgtaaattt cgagttttgc ctcagccaac taatctcgca | 1740 |
| accccaaaca caaagcgttt taaaaaagaa gaaattcttt ccagttctga catttgtcaa | 1800 |
| aagttagtaa atactcagga catgtcagcc tctcaggttg atgtagctgt gaaaattaat | 1860 |
| aagaaagttg tgcccctgga cttttctatg agttctttag ctaaacgaat aaagcagtta | 1920 |
| catcatgaag cacagcaaag tgaaggggaa cagaattaca ggaagtttag ggcaaagatt | 1980 |
| tgtcctggag aaaatcaagc agccgaagat gaactaagaa aagagataag taaaacgatg | 2040 |
| tttgcagaaa tggaaatcat tggtcagttt aacctgggat ttataataac caaactgaat | 2100 |
| gaggatatct tcatagtgga ccagcatgcc acggacgaga gtataacctt cgagatgctg | 2160 |
| cagcagcaca ccgtgctcca ggggcagagg ctcatagcac ctcagactct caacttaact | 2220 |
| gctgttaatg aagctgttct gatagaaaat ctggaaatat ttagaaagaa tggctttgat | 2280 |
| tttgttatcg atgaaaatgc tccagtcact gaaagggcta aactgatttc cttgccaact | 2340 |
| agtaaaaact ggaccttcgg accccaggac gtcgatgaac tgatcttcat gctgagcgac | 2400 |
| agccctgggg tcatgtgccg gccttccgga gtcaagcaga tgtttgcctc cagagcctgc | 2460 |
| cggaagtcgg tgatgattgg gactgctctt aacacaagcg agatgaagaa actgatcacc | 2520 |

```
cacatggggg agatggacca ccccctggaac tgtccccatg gaaggccaac catgagacac    2580
atcgccaacc tgggtgtcat ttctcagaac tgaccgtagt cactgtatgg aataattggt    2640
tttatcgcag attttatgt tttgaaagac agagtcttca ctaaccttt ttgttttaaa      2700 atgaaacctg ctacttaaaa aaatacaca tcacacccat ttaaaagtga tcttgagaac     2760
cttttcaaac c                                                          2771
```

<210> SEQ ID NO 9
<211> LENGTH: 932
<212> TYPE: PRT
<213> ORGANISM: Homo sapiens

<400> SEQUENCE: 9

```
Met Lys Gln Leu Pro Ala Ala Thr Val Arg Leu Leu Ser Ser Ser Gln
  1               5                  10                  15

Ile Ile Thr Ser Val Val Ser Val Val Lys Glu Leu Ile Glu Asn Ser
             20                  25                  30

Leu Asp Ala Gly Ala Thr Ser Val Asp Val Lys Leu Glu Asn Tyr Gly
         35                  40                  45

Phe Asp Lys Ile Glu Val Arg Asp Asn Gly Glu Gly Ile Lys Ala Val
     50                  55                  60

Asp Ala Pro Val Met Ala Met Lys Tyr Tyr Thr Ser Lys Ile Asn Ser
 65                  70                  75                  80

His Glu Asp Leu Glu Asn Leu Thr Thr Tyr Gly Phe Arg Gly Glu Ala
                 85                  90                  95

Leu Gly Ser Ile Cys Cys Ile Ala Glu Val Leu Ile Thr Thr Arg Thr
            100                 105                 110

Ala Ala Asp Asn Phe Ser Thr Gln Tyr Val Leu Asp Gly Ser Gly His
        115                 120                 125

Ile Leu Ser Gln Lys Pro Ser His Leu Gly Gln Gly Thr Thr Val Thr
    130                 135                 140

Ala Leu Arg Leu Phe Lys Asn Leu Pro Val Arg Lys Gln Phe Tyr Ser
145                 150                 155                 160

Thr Ala Lys Lys Cys Lys Asp Glu Ile Lys Lys Ile Gln Asp Leu Leu
                165                 170                 175

Met Ser Phe Gly Ile Leu Lys Pro Asp Leu Arg Ile Val Phe Val His
            180                 185                 190

Asn Lys Ala Val Ile Trp Gln Lys Ser Arg Val Ser Asp His Lys Met
        195                 200                 205

Ala Leu Met Ser Val Leu Gly Thr Ala Val Met Asn Asn Met Glu Ser
    210                 215                 220

Phe Gln Tyr His Ser Glu Glu Ser Gln Ile Tyr Leu Ser Gly Phe Leu
225                 230                 235                 240

Pro Lys Cys Asp Ala Asp His Ser Phe Thr Ser Leu Ser Thr Pro Glu
                245                 250                 255

Arg Ser Phe Ile Phe Ile Asn Ser Arg Pro Val His Gln Lys Asp Ile
            260                 265                 270

Leu Lys Leu Ile Arg His His Tyr Asn Leu Lys Cys Leu Lys Glu Ser
        275                 280                 285

Thr Arg Leu Tyr Pro Val Phe Phe Leu Lys Ile Asp Val Pro Thr Ala
    290                 295                 300

Asp Val Asp Val Asn Leu Thr Pro Asp Lys Ser Gln Val Leu Leu Gln
305                 310                 315                 320
```

-continued

```
Asn Lys Glu Ser Val Leu Ile Ala Leu Glu Asn Leu Met Thr Thr Cys
            325                 330                 335
Tyr Gly Pro Leu Pro Ser Thr Asn Ser Tyr Glu Asn Asn Lys Thr Asp
            340                 345                 350
Val Ser Ala Ala Asp Ile Val Leu Ser Lys Thr Ala Glu Thr Asp Val
            355                 360                 365
Leu Phe Asn Lys Val Glu Ser Ser Gly Lys Asn Tyr Ser Asn Val Asp
    370                 375                 380
Thr Ser Val Ile Pro Phe Gln Asn Asp Met His Asn Asp Glu Ser Gly
385                 390                 395                 400
Lys Asn Thr Asp Asp Cys Leu Asn His Gln Ile Ser Ile Gly Asp Phe
            405                 410                 415
Gly Tyr Gly His Cys Ser Ser Glu Ile Ser Asn Ile Asp Lys Asn Thr
            420                 425                 430
Lys Asn Ala Phe Gln Asp Ile Ser Met Ser Asn Val Ser Trp Glu Asn
            435                 440                 445
Ser Gln Thr Glu Tyr Ser Lys Thr Cys Phe Ile Ser Ser Val Lys His
    450                 455                 460
Thr Gln Ser Glu Asn Gly Asn Lys Asp His Ile Asp Glu Ser Gly Glu
465                 470                 475                 480
Asn Glu Glu Glu Ala Gly Leu Glu Asn Ser Ser Glu Ile Ser Ala Asp
            485                 490                 495
Glu Trp Ser Arg Gly Asn Ile Leu Lys Asn Ser Val Gly Glu Asn Ile
            500                 505                 510
Glu Pro Val Lys Ile Leu Val Pro Glu Lys Ser Leu Pro Cys Lys Val
            515                 520                 525
Ser Asn Asn Asn Tyr Pro Ile Pro Glu Gln Met Asn Leu Asn Glu Asp
    530                 535                 540
Ser Cys Asn Lys Lys Ser Asn Val Ile Asp Asn Lys Ser Gly Lys Val
545                 550                 555                 560
Thr Ala Tyr Asp Leu Leu Ser Asn Arg Val Ile Lys Lys Pro Met Ser
            565                 570                 575
Ala Ser Ala Leu Phe Val Gln Asp His Arg Pro Gln Phe Leu Ile Glu
            580                 585                 590
Asn Pro Lys Thr Ser Leu Glu Asp Ala Thr Leu Gln Ile Glu Glu Leu
            595                 600                 605
Trp Lys Thr Leu Ser Glu Glu Lys Leu Lys Tyr Glu Glu Lys Ala
            610                 615                 620
Thr Lys Asp Leu Glu Arg Tyr Asn Ser Gln Met Lys Arg Ala Ile Glu
625                 630                 635                 640
Gln Glu Ser Gln Met Ser Leu Lys Asp Gly Arg Lys Ile Lys Pro
            645                 650                 655
Thr Ser Ala Trp Asn Leu Ala Gln Lys His Lys Leu Lys Thr Ser Leu
            660                 665                 670
Ser Asn Gln Pro Lys Leu Asp Glu Leu Leu Gln Ser Gln Ile Glu Lys
            675                 680                 685
Arg Arg Ser Gln Asn Ile Lys Met Val Gln Ile Pro Phe Ser Met Lys
    690                 695                 700
Asn Leu Lys Ile Asn Phe Lys Lys Gln Asn Lys Val Asp Leu Glu Glu
705                 710                 715                 720
Lys Asp Glu Pro Cys Leu Ile His Asn Leu Arg Phe Pro Asp Ala Trp
            725                 730                 735
Leu Met Thr Ser Lys Thr Glu Val Met Leu Leu Asn Pro Tyr Arg Val
```

-continued

```
              740               745               750
Glu Glu Ala Leu Leu Phe Lys Arg Leu Leu Glu Asn His Lys Leu Pro
                755               760               765
Ala Glu Pro Leu Glu Lys Pro Ile Met Leu Thr Glu Ser Leu Phe Asn
        770               775               780
Gly Ser His Tyr Leu Asp Val Leu Tyr Lys Met Thr Ala Asp Asp Gln
785               790               795               800
Arg Tyr Ser Gly Ser Thr Tyr Leu Ser Asp Pro Arg Leu Thr Ala Asn
                805               810               815
Gly Phe Lys Ile Lys Leu Ile Pro Gly Val Ser Ile Thr Glu Asn Tyr
            820               825               830
Leu Glu Ile Glu Gly Met Ala Asn Cys Leu Pro Phe Tyr Gly Val Ala
            835               840               845
Asp Leu Lys Glu Ile Leu Asn Ala Ile Leu Asn Arg Asn Ala Lys Glu
        850               855               860
Val Tyr Glu Cys Arg Pro Arg Lys Val Ile Ser Tyr Leu Glu Gly Glu
865               870               875               880
Ala Val Arg Leu Ser Arg Gln Leu Pro Met Tyr Leu Ser Lys Glu Asp
                885               890               895
Ile Gln Asp Ile Ile Tyr Arg Met Lys His Gln Phe Gly Asn Glu Ile
            900               905               910
Lys Glu Cys Val His Gly Arg Pro Phe Phe His His Leu Thr Tyr Leu
            915               920               925
Pro Glu Thr Thr
    930
```

<210> SEQ ID NO 10
<211> LENGTH: 3063
<212> TYPE: DNA
<213> ORGANISM: Homo sapiens

<400> SEQUENCE: 10

```
ggcacgagtg gctgcttgcg gctagtggat ggtaattgcc tgcctcgcgc tagcagcaag      60
ctgctctgtt aaaagcgaaa atgaaacaat tgcctgcggc aacagttcga ctcctttcaa     120
gttctcagat catcacttcg gtggtcagtg ttgtaaaaga gcttattgaa aactccttgg     180
atgctggtgc cacaagcgta gatgttaaac tggagaacta tggatttgat aaaattgagg     240
tgcgagataa cggggagggt atcaaggctg ttgatgcacc tgtaatggca atgaagtact     300
acacctcaaa aataaatagt catgaagatc ttgaaaattt gacaacttac ggttttcgtg     360
gagaagcctt ggggtcaatt tgttgtatag ctgaggtttt aattacaaca gaacggctg      420
ctgataattt tagcacccag tatgttttag atggcagtgg ccacatactt tctcagaaac     480
cttcacatct tggtcaaggt acaactgtaa ctgctttaag attatttaag aatctacctg     540
taagaaagca gttttactca actgcaaaaa atgtaaaga tgaataaaa aagatccaag      600
atctcctcat gagctttggt atccttaaac ctgacttaag gattgtcttt gtacataaca     660
aggcagttat ttggcagaaa agcagagtat cagatcacaa gatggctctc atgtcagttc     720
tggggactgc tgttatgaac aatatggaat cctttcagta ccactctgaa gaatctcaga     780
tttatctcag tggatttctt ccaaagtgtg atgcagacca ctctttcact agtctttcaa     840
caccagaaag aagtttcatc ttcataaaca gtcgaccagt acatcaaaaa gatatcttaa     900
agttaatccg acatcattac aatctgaaat gcctaaagga atctactcgt ttgtatcctg     960
ttttctttct gaaaatcgat gttcctacag ctgatgttga tgtaaattta acaccagata    1020
```

-continued

```
aaagccaagt attattacaa ataaggaat ctgttttaat tgctcttgaa aatctgatga      1080
cgacttgtta tggaccatta cctagtacaa attcttatga aaataataaa acagatgttt      1140
ccgcagctga catcgttctt agtaaaacag cagaaacaga tgtgcttttt aataaagtgg      1200
aatcatctgg aaagaattat tcaaatgtt atacttcagt cattccattc caaaatgata      1260
tgcataatga tgaatctgga aaaacactg atgattgttt aaatcaccag ataagtattg      1320
gtgactttgg ttatggtcat tgtagtagtg aaatttctaa cattgataaa aacactaaga      1380
atgcatttca ggacatttca atgagtaatg tatcatggga gaactctcag acggaatata      1440
gtaaaacttg ttttataagt tccgttaagc acacccagtc agaaaatggc aataaagacc      1500
atatagatga gagtggggaa aatgaggaag aagcaggtct tgaaaactct tcggaaattt      1560
ctgcagatga gtggagcagg ggaaatatac ttaaaaattc agtgggagag aatattgaac      1620
ctgtgaaaat tttagtgcct gaaaaaagtt taccatgtaa agtaagtaat aataattatc      1680
caatccctga acaaatgaat cttaatgaag attcatgtaa caaaaaatca aatgtaatag      1740
ataataaatc tggaaaagtt acagcttatg atttacttag caatcgagta atcaagaaac      1800
ccatgtcagc aagtgctctt tttgttcaag atcatcgtcc tcagtttctc atagaaaatc      1860
ctaagactag tttagaggat gcaacactac aaattgaaga actgtggaag acattgagtg      1920
aagaggaaaa actgaaatat gaagagaagg ctactaaaga cttggaacga tacaatagtc      1980
aaatgaagag agccattgaa caggagtcac aaatgtcact aaaagatggc agaaaaaaga      2040
taaaacccac cagcgcatgg aatttggccc agaagcacaa gttaaaaacc tcattatcta      2100
atcaaccaaa acttgatgaa ctccttcagt cccaaattga aaaagaagg agtcaaaata      2160 ttaaaatggt acagatcccc ttttctatga aaacttaaa aataaatttt aagaaacaaa      2220
acaaagttga cttagaagag aaggatgaac cttgcttgat ccacaatctc aggtttcctg      2280
atgcatggct aatgacatcc aaaacagagg taatgttatt aaatccatat agagtagaag      2340
aagccctgct atttaaaaga cttcttgaga atcataaact tcctgcagag ccactggaaa      2400
agccaattat gttaacagag agtctttta atggatctca ttatttagac gttttatata      2460
aaatgacagc agatgaccaa agatacagtg gatcaactta cctgtctgat cctcgtctta      2520
cagcgaatgg tttcaagata aaattgatac caggagtttc aattactgaa aattacttgg      2580
aaatagaagg aatggctaat tgtctcccat tctatggagt agcagattta aaagaaattc      2640
ttaatgctat attaaacaga aatgcaaagg aagtttatga atgtagacct cgcaaagtga      2700
taagttattt agagggagaa gcagtgcgtc tatccagaca attacccatg tacttatcaa      2760
aagaggacat ccaagacatt atctacagaa tgaagcacca gtttggaaat gaattaaag      2820 agtgtgttca tggtcgccca ttttttcatc atttaaccta tcttccagaa actacatgat      2880
taaatatgtt taagaagatt agttaccatt gaaattggtt ctgtcataaa acagcatgag      2940
tctggtttta aattatcttt gtattatgtg tcacatggtt attttttaaa tgaggattca      3000
ctgacttgtt tttatattga aaaagttcc acgtattgta gaaaacgtaa ataaactaat      3060
aac                                                                   3063
```

<210> SEQ ID NO 11
<211> LENGTH: 934
<212> TYPE: PRT
<213> ORGANISM: Homo sapiens

<400> SEQUENCE: 11

-continued

```
Met Ala Val Gln Pro Lys Glu Thr Leu Gln Leu Glu Ser Ala Ala Glu
 1               5                  10                  15

Val Gly Phe Val Arg Phe Phe Gln Gly Met Pro Glu Lys Pro Thr Thr
            20                  25                  30

Thr Val Arg Leu Phe Asp Arg Gly Asp Phe Tyr Thr Ala His Gly Glu
            35                  40                  45

Asp Ala Leu Leu Ala Ala Arg Glu Val Phe Lys Thr Gln Gly Val Ile
    50                  55                  60

Lys Tyr Met Gly Pro Ala Gly Ala Lys Asn Leu Gln Ser Val Val Leu
65                  70                  75                  80

Ser Lys Met Asn Phe Glu Ser Phe Val Lys Asp Leu Leu Leu Val Arg
                85                  90                  95

Gln Tyr Arg Val Glu Val Tyr Lys Asn Arg Ala Gly Asn Lys Ala Ser
            100                 105                 110

Lys Glu Asn Asp Trp Tyr Leu Ala Tyr Lys Ala Ser Pro Gly Asn Leu
            115                 120                 125

Ser Gln Phe Glu Asp Ile Leu Phe Gly Asn Asn Asp Met Ser Ala Ser
    130                 135                 140

Ile Gly Val Val Gly Val Lys Met Ser Ala Val Asp Gly Gln Arg Gln
145                 150                 155                 160

Val Gly Val Gly Tyr Val Asp Ser Ile Gln Arg Lys Leu Gly Leu Cys
            165                 170                 175

Glu Phe Pro Asp Asn Asp Gln Phe Ser Asn Leu Glu Ala Leu Leu Ile
            180                 185                 190

Gln Ile Gly Pro Lys Glu Cys Val Leu Pro Gly Gly Glu Thr Ala Gly
            195                 200                 205

Asp Met Gly Lys Leu Arg Gln Ile Ile Gln Arg Gly Gly Ile Leu Ile
    210                 215                 220

Thr Glu Arg Lys Lys Ala Asp Phe Ser Thr Lys Asp Ile Tyr Gln Asp
225                 230                 235                 240

Leu Asn Arg Leu Leu Lys Gly Lys Gly Glu Gln Met Asn Ser Ala
            245                 250                 255

Val Leu Pro Glu Met Glu Asn Gln Val Ala Val Ser Ser Leu Ser Ala
            260                 265                 270

Val Ile Lys Phe Leu Glu Leu Leu Ser Asp Asp Ser Asn Phe Gly Gln
            275                 280                 285

Phe Glu Leu Thr Thr Phe Asp Phe Ser Gln Tyr Met Lys Leu Asp Ile
    290                 295                 300

Ala Ala Val Arg Ala Leu Asn Leu Phe Gln Gly Ser Val Glu Asp Thr
305                 310                 315                 320

Thr Gly Ser Gln Ser Leu Ala Ala Leu Leu Asn Lys Cys Lys Thr Pro
            325                 330                 335

Gln Gly Gln Arg Leu Val Asn Gln Trp Ile Lys Gln Pro Leu Met Asp
            340                 345                 350

Lys Asn Arg Ile Glu Glu Arg Leu Asn Leu Val Glu Ala Phe Val Glu
            355                 360                 365

Asp Ala Glu Leu Arg Gln Thr Leu Gln Glu Asp Leu Leu Arg Arg Phe
    370                 375                 380

Pro Asp Leu Asn Arg Leu Ala Lys Lys Phe Gln Arg Gln Ala Ala Asn
385                 390                 395                 400

Leu Gln Asp Cys Tyr Arg Leu Tyr Gln Gly Ile Asn Gln Leu Pro Asn
            405                 410                 415

Val Ile Gln Ala Leu Glu Lys His Glu Gly Lys His Gln Lys Leu Leu
```

-continued

```
            420              425              430
Leu Ala Val Phe Val Thr Pro Leu Thr Asp Leu Arg Ser Asp Phe Ser
            435              440              445
Lys Phe Gln Glu Met Ile Glu Thr Thr Leu Asp Met Asp Gln Val Glu
450              455              460
Asn His Glu Phe Leu Val Lys Pro Ser Phe Asp Pro Asn Leu Ser Glu
465              470              475              480
Leu Arg Glu Ile Met Asn Asp Leu Glu Lys Lys Met Gln Ser Thr Leu
            485              490              495
Ile Ser Ala Ala Arg Asp Leu Gly Leu Asp Pro Gly Lys Gln Ile Lys
            500              505              510
Leu Asp Ser Ser Ala Gln Phe Gly Tyr Tyr Phe Arg Val Thr Cys Lys
            515              520              525
Glu Glu Lys Val Leu Arg Asn Asn Lys Asn Phe Ser Thr Val Asp Ile
            530              535              540
Gln Lys Asn Gly Val Lys Phe Thr Asn Ser Lys Leu Thr Ser Leu Asn
545              550              555              560
Glu Glu Tyr Thr Lys Asn Lys Thr Glu Tyr Glu Glu Ala Gln Asp Ala
            565              570              575
Ile Val Lys Glu Ile Val Asn Ile Ser Ser Gly Tyr Val Glu Pro Met
            580              585              590
Gln Thr Leu Asn Asp Val Leu Ala Gln Leu Asp Ala Val Val Ser Phe
            595              600              605
Ala His Val Ser Asn Gly Ala Pro Val Pro Tyr Val Arg Pro Ala Ile
            610              615              620
Leu Glu Lys Gly Gln Gly Arg Ile Ile Leu Lys Ala Ser Arg His Ala
625              630              635              640
Cys Val Glu Val Gln Asp Glu Ile Ala Phe Ile Pro Asn Asp Val Tyr
            645              650              655
Phe Glu Lys Asp Lys Gln Met Phe His Ile Ile Thr Gly Pro Asn Met
            660              665              670
Gly Gly Lys Ser Thr Tyr Ile Arg Gln Thr Gly Val Ile Val Leu Met
            675              680              685
Ala Gln Ile Gly Cys Phe Val Pro Cys Glu Ser Ala Glu Val Ser Ile
            690              695              700
Val Asp Cys Ile Leu Ala Arg Val Gly Ala Gly Asp Ser Gln Leu Lys
705              710              715              720
Gly Val Ser Thr Phe Met Ala Glu Met Leu Glu Thr Ala Ser Ile Leu
            725              730              735
Arg Ser Ala Thr Lys Asp Ser Leu Ile Ile Ile Asp Glu Leu Gly Arg
            740              745              750
Gly Thr Ser Thr Tyr Asp Gly Phe Gly Leu Ala Trp Ala Ile Ser Glu
            755              760              765
Tyr Ile Ala Thr Lys Ile Gly Ala Phe Cys Met Phe Ala Thr His Phe
            770              775              780
His Glu Leu Thr Ala Leu Ala Asn Gln Ile Pro Thr Val Asn Asn Leu
785              790              795              800
His Val Thr Ala Leu Thr Thr Glu Glu Thr Leu Thr Met Leu Tyr Gln
            805              810              815
Val Lys Lys Gly Val Cys Asp Gln Ser Phe Gly Ile His Val Ala Glu
            820              825              830
Leu Ala Asn Phe Pro Lys His Val Ile Glu Cys Ala Lys Gln Lys Ala
            835              840              845
```

```
Leu Glu Leu Glu Glu Phe Gln Tyr Ile Gly Ser Gln Gly Tyr Asp
    850                 855                 860

Ile Met Glu Pro Ala Ala Lys Lys Cys Tyr Leu Glu Arg Glu Gln Gly
865                 870                 875                 880

Glu Lys Ile Ile Gln Glu Phe Leu Ser Lys Val Lys Gln Met Pro Phe
                885                 890                 895

Thr Glu Met Ser Glu Glu Asn Ile Thr Ile Lys Leu Lys Gln Leu Lys
                900                 905                 910

Ala Glu Val Ile Ala Lys Asn Asn Ser Phe Val Asn Glu Ile Ile Ser
            915                 920                 925

Arg Ile Lys Val Thr Thr
    930

<210> SEQ ID NO 12
<211> LENGTH: 3145
<212> TYPE: DNA
<213> ORGANISM: Homo sapiens

<400> SEQUENCE: 12
ggcgggaaac agcttagtgg gtgtggggtc gcgcattttc ttcaaccagg aggtgaggag     60
gtttcgacat ggcggtgcag ccgaaggaga cgctgcagtt ggagagcgcg gccgaggtcg    120
gcttcgtgcg cttctttcag ggcatgccgg agaagccgac caccacagtg cgccttttcg    180
accgggcgga cttctatacg gcgcacggcg aggacgcgct gctggccgcc cgggaggtgt    240
tcaagaccca gggggtgatc aagtacatgg ggccggcagg agcaaagaat ctgcagagtg    300
ttgtgcttag taaaatgaat tttgaatctt ttgtaaaaga tcttcttctg gttcgtcagt    360
atagagttga agtttataag aatagagctg gaaataaggc atccaaggag aatgattggt    420
atttggcata taaggcttct cctggcaatc tctctcagtt tgaagacatt ctctttggta    480
acaatgatat gtcagcttcc attggtgttg tgggtgttaa aatgtccgca gttgatggcc    540
agagacaggt tggagttggg tatgtggatt ccatacagag gaaactagga ctgtgtgaat    600
tccctgataa tgatcagttc tccaatcttg aggctctcct catccagatt ggaccaaagg    660
aatgtgtttt acccggagga gagactgctg gagacatggg gaaactgaga cagataattc    720
aaagaggagg aattctgatc acagaaagaa aaaagctga cttttccaca aagacattt    780
atcaggacct caaccggttg ttgaaaggca aaaaggaga gcagatgaat agtgctgtat    840
tgccagaaat ggagaatcag gttgcagttt catcactgtc tgcggtaatc aagttttag    900
aactcttatc agatgattcc aactttggac agtttgaact gactacttt gacttcagcc    960
agtatatgaa attggatatt gcagcagtca gagcccttaa cctttttcag ggttctgttg   1020
aagataccac tggctctcag tctctggctg ccttgctgaa taagtgtaaa acccctcaag   1080
gacaaagact tgttaaccag tggattaagc agcctctcat ggataagaac agaatagagg   1140
agagattgaa tttagtggaa gcttttgtag aagatgcaga attgaggcag actttacaag   1200
aagatttact tcgtcgattc ccagatctta accgacttgc caagaagttt caaagacaag   1260
cagcaaactt acaagattgt taccgactct atcagggtat aaatcaacta cctaatgtta   1320
tacaggctct ggaaaaacat gaaggaaaac accagaaatt attgttggca gttttttgtga   1380
ctcctcttac tgatcttcgt tctgacttct ccaagtttca ggaaatgata gaaacaactt   1440
tagatatgga tcaggtggaa aaccatgaat tccttgtaaa accttcattt gatcctaatc   1500
tcagtgaatt aagagaaata atgaatgact tggaaaagaa gatgcagtca acattaataa   1560
```

-continued

```
gtgcagccag agatcttggc ttggaccctg gcaaacagat taaactggat tccagtgcac    1620
agtttggata ttactttcgt gtaacctgta aggaagaaaa agtccttcgt aacaataaaa    1680
actttagtac tgtagatatc cagaagaatg gtgttaaatt taccaacagc aaattgactt    1740
ctttaaatga agagtatacc aaaaataaaa cagaatatga agaagcccag gatgccattg    1800
ttaaagaaat tgtcaatatt tcttcaggct atgtagaacc aatgcagaca ctcaatgatg    1860
tgttagctca gctagatgct gttgtcagct ttgctcacgt gtcaaatgga gcacctgttc    1920
catatgtacg accagccatt ttggagaaag gacaaggaag aattatatta aaagcatcca    1980
ggcatgcttg tgttgaagtt caagatgaaa ttgcatttat tcctaatgac gtatactttg    2040
aaaaagataa acagatgttc cacatcatta ctggccccaa tatgggaggt aaatcaacat    2100
atattcgaca aactggggtg atagtactca tggcccaaat tgggtgtttt gtgccatgtg    2160
agtcagcaga agtgtccatt gtggactgca tcttagcccg agtaggggct ggtgacagtc    2220
aattgaaagg agtctccacg ttcatggctg aaatgttgga aactgcttct atcctcaggt    2280
ctgcaaccaa agattcatta ataatcatag atgaattggg aagaggaact tctacctacg    2340
atggatttgg gttagcatgg gctatatcag aatacattgc aacaaagatt ggtgcttttt    2400
gcatgtttgc aacccatttt catgaactta ctgccttggc caatcagata ccaactgtta    2460
ataatctaca tgtcacagca ctcaccactg aagagacctt aactatgctt tatcaggtga    2520
agaaaggtgt ctgtgatcaa agttttggga ttcatgttgc agagcttgct aatttcccta    2580
agcatgtaat agagtgtgct aaacagaaag ccctggaact tgaggagttt cagtatattg    2640
gagaatcgca aggatatgat atcatggaac cagcagcaaa gaagtgctat ctggaaagag    2700
agcaaggtga aaaaattatt caggagttcc tgtccaaggt gaaacaaatg ccctttactg    2760
aaatgtcaga agaaacatc acaataaagt taaaacagct aaaagctgaa gtaatagcaa    2820
agaataatag ctttgtaaat gaaatcattt cacgaataaa agttactacg tgaaaaatcc    2880
cagtaatgga atgaaggtaa tattgataag ctattgtctg taatagtttt atattgtttt    2940
atattaaccc ttttccata gtgttaactg tcagtgccca tgggctatca acttaataag    3000
atatttagta atatttact ttgaggacat tttcaaagat tttatttttg aaaaatgaga    3060
gctgtaactg aggactgttt gcaattgaca taggcaataa taagtgatgt gctgaatttt    3120
ataaataaaa tcatgtagtt tgtgg                                          3145
```

<210> SEQ ID NO 13
<211> LENGTH: 756
<212> TYPE: PRT
<213> ORGANISM: Homo sapiens

<400> SEQUENCE: 13

```
Met Ser Phe Val Ala Gly Val Ile Arg Arg Leu Asp Glu Thr Val Val
  1               5                  10                  15

Asn Arg Ile Ala Ala Gly Glu Val Ile Gln Arg Pro Ala Asn Ala Ile
                 20                  25                  30

Lys Glu Met Ile Glu Asn Cys Leu Asp Ala Lys Ser Thr Ser Ile Gln
         35                  40                  45

Val Ile Val Lys Glu Gly Gly Leu Lys Leu Ile Gln Ile Gln Asp Asn
     50                  55                  60

Gly Thr Gly Ile Arg Lys Glu Asp Leu Asp Ile Val Cys Glu Arg Phe
 65                  70                  75                  80

Thr Thr Ser Lys Leu Gln Ser Phe Glu Asp Leu Ala Ser Ile Ser Thr
                 85                  90                  95
```

```
Tyr Gly Phe Arg Gly Glu Ala Leu Ala Ser Ile Ser His Val Ala His
            100                 105                 110

Val Thr Ile Thr Thr Lys Thr Ala Asp Gly Lys Cys Ala Tyr Arg Ala
            115                 120                 125

Ser Tyr Ser Asp Gly Lys Leu Lys Ala Pro Pro Lys Pro Cys Ala Gly
            130                 135                 140

Asn Gln Gly Thr Gln Ile Thr Val Glu Asp Leu Phe Tyr Asn Ile Ala
145                 150                 155                 160

Thr Arg Arg Lys Ala Leu Lys Asn Pro Ser Glu Glu Tyr Gly Lys Ile
                165                 170                 175

Leu Glu Val Val Gly Arg Tyr Ser Val His Asn Ala Gly Ile Ser Phe
            180                 185                 190

Ser Val Lys Lys Gln Gly Glu Thr Val Ala Asp Val Arg Thr Leu Pro
            195                 200                 205

Asn Ala Ser Thr Val Asp Asn Ile Arg Ser Ile Phe Gly Asn Ala Val
            210                 215                 220

Ser Arg Glu Leu Ile Glu Ile Gly Cys Glu Asp Lys Thr Leu Ala Phe
225                 230                 235                 240

Lys Met Asn Gly Tyr Ile Ser Asn Ala Asn Tyr Ser Val Lys Lys Cys
                245                 250                 255

Ile Phe Leu Leu Phe Ile Asn His Arg Leu Val Glu Ser Thr Ser Leu
            260                 265                 270

Arg Lys Ala Ile Glu Thr Val Tyr Ala Ala Tyr Leu Pro Lys Asn Thr
            275                 280                 285

His Pro Phe Leu Tyr Leu Ser Leu Glu Ile Ser Pro Gln Asn Val Asp
            290                 295                 300

Val Asn Val His Pro Thr Lys His Glu Val His Phe Leu His Glu Glu
305                 310                 315                 320

Ser Ile Leu Glu Arg Val Gln Gln His Ile Glu Ser Lys Leu Leu Gly
                325                 330                 335

Ser Asn Ser Ser Arg Met Tyr Phe Thr Gln Thr Leu Leu Pro Gly Leu
            340                 345                 350

Ala Gly Pro Ser Gly Glu Met Val Lys Ser Thr Thr Ser Leu Thr Ser
            355                 360                 365

Ser Ser Thr Ser Gly Ser Ser Asp Lys Val Tyr Ala His Gln Met Val
370                 375                 380

Arg Thr Asp Ser Arg Glu Gln Lys Leu Asp Ala Phe Leu Gln Pro Leu
385                 390                 395                 400

Ser Lys Pro Leu Ser Ser Gln Pro Gln Ala Ile Val Thr Glu Asp Lys
            405                 410                 415

Thr Asp Ile Ser Ser Gly Arg Ala Arg Gln Gln Asp Glu Glu Met Leu
            420                 425                 430

Glu Leu Pro Ala Pro Ala Glu Val Ala Ala Lys Asn Gln Ser Leu Glu
            435                 440                 445

Gly Asp Thr Thr Lys Gly Thr Ser Glu Met Ser Glu Lys Arg Gly Pro
450                 455                 460

Thr Ser Ser Asn Pro Arg Lys Arg His Arg Glu Asp Ser Asp Val Glu
465                 470                 475                 480

Met Val Glu Asp Asp Ser Arg Lys Glu Met Thr Ala Ala Cys Thr Pro
                485                 490                 495

Arg Arg Arg Ile Ile Asn Leu Thr Ser Val Leu Ser Leu Gln Glu Glu
            500                 505                 510
```

-continued

```
Ile Asn Glu Gln Gly His Glu Val Leu Arg Glu Met Leu His Asn His
            515                 520                 525
Ser Phe Val Gly Cys Val Asn Pro Gln Trp Ala Leu Ala Gln His Gln
        530                 535                 540
Thr Lys Leu Tyr Leu Leu Asn Thr Thr Lys Leu Ser Glu Glu Leu Phe
545                 550                 555                 560
Tyr Gln Ile Leu Ile Tyr Asp Phe Ala Asn Phe Gly Val Leu Arg Leu
                565                 570                 575
Ser Glu Pro Ala Pro Leu Phe Asp Leu Ala Met Leu Ala Leu Asp Ser
            580                 585                 590
Pro Glu Ser Gly Trp Thr Glu Glu Asp Gly Pro Lys Glu Gly Leu Ala
        595                 600                 605
Glu Tyr Ile Val Glu Phe Leu Lys Lys Lys Ala Glu Met Leu Ala Asp
610                 615                 620
Tyr Phe Ser Leu Glu Ile Asp Glu Glu Gly Asn Leu Ile Gly Leu Pro
625                 630                 635                 640
Leu Leu Ile Asp Asn Tyr Val Pro Pro Leu Glu Gly Leu Pro Ile Phe
                645                 650                 655
Ile Leu Arg Leu Ala Thr Glu Val Asn Trp Asp Glu Glu Lys Glu Cys
            660                 665                 670
Phe Glu Ser Leu Ser Lys Glu Cys Ala Met Phe Tyr Ser Ile Arg Lys
        675                 680                 685
Gln Tyr Ile Ser Glu Glu Ser Thr Leu Ser Gly Gln Gln Ser Glu Val
    690                 695                 700
Pro Gly Ser Ile Pro Asn Ser Trp Lys Trp Thr Val Glu His Ile Val
705                 710                 715                 720
Tyr Lys Ala Leu Arg Ser His Ile Leu Pro Pro Lys His Phe Thr Glu
                725                 730                 735
Asp Gly Asn Ile Leu Gln Leu Ala Asn Leu Pro Asp Leu Tyr Lys Val
            740                 745                 750
Phe Glu Arg Cys
        755

<210> SEQ ID NO 14
<211> LENGTH: 2484
<212> TYPE: DNA
<213> ORGANISM: Homo sapiens

<400> SEQUENCE: 14
cttggctctt ctggcgccaa aatgtcgttc gtggcagggg ttattcggcg gctggacgag     60
acagtggtga accgcatcgc ggcgggggaa gttatccagc ggccagctaa tgctatcaaa    120
gagatgattg agaactgttt agatgcaaaa tccacaagta ttcaagtgat tgttaaagag    180
ggaggcctga agttgattca gatccaagac aatggcaccg ggatcaggaa agaagatctg    240
gatattgtat gtgaaaggtt cactactagt aaactgcagt cctttgagga tttagccagt    300
atttctacct atggctttcg aggtgaggct ttggccagca taagccatgt ggctcatgtt    360
actattacaa cgaaaacagc tgatggaaag tgtgcataca gagcaagtta ctcagatgga    420
aaactgaaag cccctcctaa accatgtgct ggcaatcaag ggacccagat cacggtggag    480 gaccttttt acaacatagc cacgaggaga aaagctttaa aaaatccaag tgaagaatat    540
gggaaaattt tggaagttgt tggcaggtat tcagtacaca atgcaggcat tagtttctca    600
gttaaaaaac aaggagagac agtagctgat gttaggacac tacccaatgc ctcaaccgtg    660
gacaatattc gctccatctt tggaaatgct gttagtcgag aactgatagaa aattggatgt    720
```

-continued

```
gaggataaaa ccctagcctt caaaatgaat ggttacatat ccaatgcaaa ctactcagtg      780
aagaagtgca tcttcttact cttcatcaac catcgtctgg tagaatcaac ttccttgaga      840
aaagccatag aaacagtgta tgcagcctat ttgcccaaaa acacacaccc attcctgtac      900
ctcagtttag aaatcagtcc ccagaatgtg atgttaatg tgcaccccac aaagcatgaa       960
gttcacttcc tgcacgagga gagcatcctg agcgggtgc agcagcacat cgagagcaag      1020
ctcctgggct ccaattcctc caggatgtac ttcacccaga cttttgctacc aggacttgct     1080 ggcccctctg gggagatggt taaatccaca acaagtctga cctcgtcttc tacttctgga     1140
agtagtgata aggtctatgc ccaccagatg gttcgtacag attcccggga acagaagctt     1200
gatgcatttc tgcagcctct gagcaaaccc ctgtccagtc agcccaggc cattgtcaca      1260 gaggataaga cagatatttc tagtggcagg gctaggcagc aagatgagga gatgcttgaa     1320
ctcccagccc ctgctgaagt ggctgccaaa aatcagagct ggaggggga tacaacaaag      1380 gggacttcag aaatgtcaga agagagga cctacttcca gcaaccccag aaagagacat       1440
cgggaagatt ctgatgtgga aatggtggaa gatgattccc gaaaggaaat gactgcagct     1500
tgtacccccc ggagaaggat cattaacctc actagtgttt tgagtctcca ggaagaaatt     1560
aatgagcagg gacatgaggt tctccgggag atgttgcata accactcctt cgtgggctgt     1620
gtgaatcctc agtgggcctt ggcacagcat caaaccaagt tataccttct caacaccacc     1680
aagcttagtg aagaactgtt ctaccagata ctcatttatg attttgccaa ttttggtgtt     1740
ctcaggttat cggagccagc accgctcttt gaccttgcca tgcttgcctt agatagtcca     1800
gagagtggct ggacagagga agatggtccc aaagaaggac ttgctgaata cattgttgag     1860
tttctgaaga agaaggctga gatgcttgca gactatttct ctttggaaat tgatgaggaa     1920
gggaacctga ttggattacc ccttctgatt gacaactatg tgccccttt ggagggactg      1980 cctatcttca ttcttcgact agccactgag gtgaattggg acgaagaaaa ggaatgtttt     2040
gaaagcctca gtaaagaatg cgctatgttc tattccatcc ggaagcagta catatctgag     2100
gagtcgaccc tctcaggcca gcagagtgaa gtgcctggct ccattccaaa ctcctggaag     2160
tggactgtgg aacacattgt ctataaagcc ttgcgctcac acattctgcc tcctaaacat     2220
ttcacagaag atggaaatat cctgcagctt gctaacctgc ctgatctata caagtctttt     2280
gagaggtgtt aaatatggtt atttatgcac tgtgggatgt gttcttcttt ctctgtattc     2340
cgatacaaag tgttgtatca aagtgtgata tacaaagtgt accaacataa gtgttggtag     2400
cacttaagac ttatacttgc cttctgatag tattcctta tacacagtgg attgattata      2460
aataaataga tgtgtcttaa cata                                            2484
```

<210> SEQ ID NO 15
<211> LENGTH: 133
<212> TYPE: PRT
<213> ORGANISM: Homo sapiens

<400> SEQUENCE: 15

```
Met Lys Gln Leu Pro Ala Ala Thr Val Arg Leu Leu Ser Ser Ser Gln
 1               5                  10                  15

Ile Ile Thr Ser Val Val Ser Val Val Lys Glu Leu Ile Glu Asn Ser
            20                  25                  30

Leu Asp Ala Gly Ala Thr Ser Val Asp Val Lys Leu Glu Asn Tyr Gly
        35                  40                  45

Phe Asp Lys Ile Glu Val Arg Asp Asn Gly Glu Gly Ile Lys Ala Val
```

```
                50                  55                  60
Asp Ala Pro Val Met Ala Met Lys Tyr Tyr Thr Ser Lys Ile Asn Ser
 65                  70                  75                  80

His Glu Asp Leu Glu Asn Leu Thr Thr Tyr Gly Phe Arg Gly Glu Ala
                 85                  90                  95

Leu Gly Ser Ile Cys Cys Ile Ala Glu Val Leu Ile Thr Thr Arg Thr
            100                 105                 110

Ala Ala Asp Asn Phe Ser Thr Gln Tyr Val Leu Asp Gly Ser Gly His
            115                 120                 125

Ile Leu Ser Gln Lys
    130

<210> SEQ ID NO 16
<211> LENGTH: 426
<212> TYPE: DNA
<213> ORGANISM: Homo sapiens

<400> SEQUENCE: 16
cgaggcggat cgggtgttgc atccatggag cgagctgaga gctcgagtac agaacctgct     60
aaggccatca aacctattga tcggaagtca gtccatcaga tttgctctgg gcaggtggta    120
ctgagtctaa gcactgcggt aaaggagtta gtagaaaaca gtctggatgc tggtgccact    180
aatattgatc taaagcttaa ggactatgga gtggatctta ttgaagtttc agacaatgga    240
tgtggggtag aagaagaaaa cttcgaaggc ttaactctga aacatcacac atctaagatt    300
caagagtttg ccgacctaac tcaggttgaa acttttggct ttcgggggga agctctgagc    360
tcactttgtg cactgagcga tgtcaccatt tctacctgcc acgcatcggc gaaggttgga    420
acttga                                                              426

<210> SEQ ID NO 17
<211> LENGTH: 181
<212> TYPE: DNA
<213> ORGANISM: Artificial Sequence
<220> FEATURE:
<223> OTHER INFORMATION: Description of Artificial Sequence:expression
      cassette

<400> SEQUENCE: 17
aagcttccat gtacaggatg caactcctgt cttgcattgc actaagtctt gcacttgtca     60
caaacagtgc acaaaagctg gagctccacc gcggtggcgg ccgctctaga actagtggat    120
cccccggggc tgcaggaatt cgatatcaag ccaccatcac catcaccact agtagaagct    180
t                                                                   181
```

METHOD FOR GENERATING GENETICALLY ALTERED ANTIGENS

TECHNICAL FIELD OF THE INVENTION

The invention is related to the area of genetic alterations of antigens as potent vaccines. In particular it is related to the field of mutagenesis.

BACKGROUND OF THE INVENTION

The use of vaccines to build immunity against foreign and/or endogenous polypeptides provides an effective and selective strategy for treating the underlying cause of disease. In particular is the use of killed viruses such as the polio mellitus and the Hepatitis B virus (John T. J. (2000) *New Engl. J. Med.* 14:806–807). Standard methods for generating vaccines against candidate pathogenic organisms or molecules are known by those skilled in the art. Vaccines for human use are developed in animal models to survey for the ability of killed or defective whole agents such as parasites, viruses or recombinant polypeptides to cause immunity against infection of the pathogenic agent (Boyce T. G. et al. (2000) *Vaccine* 19:217–226). Briefly, rodents such as mice or rats are injected with a purified antigen in the presence of adjuvant to generate an immune response (Boyce T. G. et al. (2000) *Vaccine* 19:217–226). Unfortunately, not all antigens are capable of eliciting a strong immune response when injected into a host organism (Hoshino Y. and A. Z. Kapikian (2000) *J. Health Popul. Nutr.* 18:5–14; Orenstein W.A. et al. (2000) *Am. J. Public Health* 90:1521–525; Lechmann M. and T. J. Liang (2000) *Semin. Liver Dis.* 20:211–226). While the reasons for the lack of immune response are not clear, some factors, such as the lack of T-cell epitopes which are important for stimulating cellular-mediated immune responses, may be absent within a given antigen (Ausiello C. M. et al. (1999) *Infect. Immun.*67:4064–4071; Brosstoff S. (1995) *Adv. Exp. Med. Biol.* 383:249–254). In the case of parasitic infections, the development of effective vaccines has been hampered by the presence of many different developmental stages that occur within an infected host and that a diverse array of allelic forms occurs within genes encoding for prominent surface antigens (MALARIA OBSTACLES AND OPPORTUNITIES, Oaks, S. C. et al., Eds., National Academy Press, p 1, 1991; Anders, R. F. "Vaccines Against Asexual Blood Stages of *Plasmodium falciparum*" NEW GENERATION VACCINES, 2nd Ed., Anders, R. F., pp. 1035–1055, 1997). It is believed by many skilled in the art that the generation of highly antigenic polypeptides may overcome these limitations and produce a protective immune response to pathogens (McLeod R. et al. (1995) *Curr. Opin. Immunol.*7:539–552).

A method for generating diverse sequences within a polypeptide would be useful for the creation of more potent therapeutic agents. Moreover, the generation of randomly altered nucleotides and encoded polypeptide residues throughout an entire antigen molecule may result in new reagents that are: 1) more antigenic; 2) more immunogenic; and 3) have beneficial pharmacokinetic properties.

SUMMARY OF THE INVENTION

The invention described herein is directed to the use of random genetic mutation of a polypeptide in vivo by blocking the endogenous mismatch repair (MMR) activity of a host cell yielding structurally altered antigens that can be screened for antigenicity and immunogenicity in comparison to the wild type molecule. The use of mammalian cell-based high throughput screens as taught by this application will facilitate identification of randomly altered antigens that may serve as effective vaccines. Moreover, the invention describes methods for repeated in vivo genetic alterations and selection for antigens with enhanced immunogenicity and pharmacokinetic profiles.

The ability to develop and screen genetically altered mammalian cells that secrete structurally altered polypeptides in a high throughput manner provides a valuable method for creating vaccines for therapeutic development. A potential problem in generating potent vaccine antigens against endogenous to the mammalian host is the source of antigen production. In many instances recombinant polypeptides that are naturally produced by mammalian cells are generated recombinantly using insect, yeast or bacterial expression systems. These sources typically produce large amounts of proteins that are distinct from the mammalian-produced polypeptides, and may differ from the natural protein due to altered folding or altered post-translational modifications such as hyperglycosylation. The invention described herein is directed to the creation of genetically altered mammalian cell hosts that produce structurally altered polypeptides as vaccine agents via the blockade of MMR.

The present invention facilitates the generation of highly antigenic polypeptides as vaccines. The advantages of the present invention are further described in the examples and figures described herein.

The present invention provides methods for generating genetically altered antigens in vivo, whereby the antigen possesses desired biochemical property(s), such as, but not limited to, increased antigenicity and immunogenicity. One method for identifying antigens with increased antigenicity is through the screening of mismatch repair ("MMR") defective cell clones that produce desired antigens.

The invention also provides methods for rendering cells expressing a target antigen hypermutable. The cells include, but are not limited to rodent, primate, human, plant, yeast or bacterial cells. The antigens can be generated from endogenous genes or from introduced transgenes.

The invention also provides methods for generating genetically altered cell lines that express antigenic polypeptides.

In some embodiments, the invention provides methods for generating genetically altered cell lines that produce immunogenic polypeptides.

In other embodiments, the invention provides methods for producing an antigen expression cassette for high throughput screening of altered polypeptides in vivo.

In other embodiments, the invention provides methods of mutating a gene of interest in a mismatch repair defective cell.

In some embodiments, the invention provides methods of creating genetically altered antigens in vivo by blocking the MMR activity of the cell host.

Still other embodiments of the invention provide methods of creating genetically altered polypeptides in vivo by transfecting genes encoding for an antigen in a MMR defective cell host.

The invention also embraces methods of creating antigens with increased immunogencity due to genetic alterations within the antigen-encoding gene by blocking endogenous MMR of the cell host.

In some embodiments, the invention provides methods of creating a library of randomly altered antigens from mammalian cells by blockade of MMR of the cell host.

In other embodiments, the invention provides methods of creating antigens with enhanced pharmacokinetic profiles due to genetic changes within the encoding gene by blocking endogenous MMR of the cell host.

The invention also provides methods of creating genetically altered antigens in MMR defective cells as vaccine agents.

In some embodiments, the invention provides methods for high throughput screening of antigens produced by MMR defective cells.

These and other objects of the invention are provided by one or more of the embodiments described below. In one embodiment of the invention, a method for making MMR defective cell lines expressing a target antigen will be provided. A polynucleotide encoding a dominant negative allele of an MMR gene is introduced into a target antigen-producing cell. The cell becomes hypermutable as a result of the introduction of the gene.

In another embodiment of the invention, an isolated hypermutable cell producing antigenic peptides is provided. The cell is defective for mismatch repair and exhibits an enhanced rate of hypermutation. The cell produces a polypeptide from a mutated gene encoding for the polypeptide.

In another embodiment of the invention, a method is provided for introducing a mutation into an endogenous gene encoding for a target polypeptide. A polynucleotide encoding a dominant negative allele of a MMR gene is introduced into a cell. The cell becomes hypermutable as a result of the introduction and expression of the MMR gene allele. The cell further comprises a gene of interest. The cell is grown and tested to determine whether the gene encoding for a polypeptide of interest harbors a mutation.

In another embodiment of the invention, a method is provided for producing a cell-based screening assay to identify antigenic proteins as vaccines. A polynucleotide encoding a dominant negative allele of a MMR gene is introduced into a cell expressing a secreted antigen. The cell becomes hypermutable as a result of the introduction of the gene. The cell is grown and conditioned medium from the cell is tested for the expression of antigenic polypeptides.

In another embodiment of the invention, a gene, or set of genes encoding for polypeptides or a combination therein, are introduced into a mammalian cell host that is defective in MMR. The cell is grown and clones are analyzed for antigens with enhanced antigenicity.

In another embodiment of the invention, a method is provided for producing a cell-based screening assay to identify antigenic proteins as vaccines. A polynucleotide encoding a secreted antigen is introduced into a naturally MMR defective cell. The gene is hypermutable as a result of the introduction of MMR deficiency. The cell is grown and conditioned medium from the cell is tested for the expression of antigenic polypeptides.

In another embodiment of the invention, a method will be provided for restoring genetic stability in a cell containing a polynucleotide encoding for a dominant negative allele of a MMR gene. The expression of the dominant negative MMR gene is suppressed and the cell restores its genetic stability including but not limited to genetic stability within the antigen-encoding genes.

In another embodiment of the invention, a method will be provided for restoring genetic stability in a cell containing a polynucleotide encoding a dominant negative allele of an MMR gene and a newly selected phenotype. The expression of the dominant negative mismatch repair gene is suppressed and the cell restores its genetic stability and the new phenotype is stable.

These and other embodiments of the invention provide the art with methods that can generate enhanced mutability in cells and animals as well as providing cells and animals harboring potentially useful mutations for the large-scale production of highly antigenic polypeptides as potent vaccines.

BRIEF DESCRIPTION OF THE DRAWINGS

FIG. 1: In situ β-galactosidase staining of TKPMS134/pCAR-OF or TKvect/pCAR-OF cells to assay for MMR defective cells containing genetically altered β-galactosidase genes. Arrows indicate Blue (β-galactosidase positive) cells.

FIG. 2: Schematic representation of sequence alterations of the β-galactosidase gene produced by MMR defective host cells

Figures 3A, 3B:
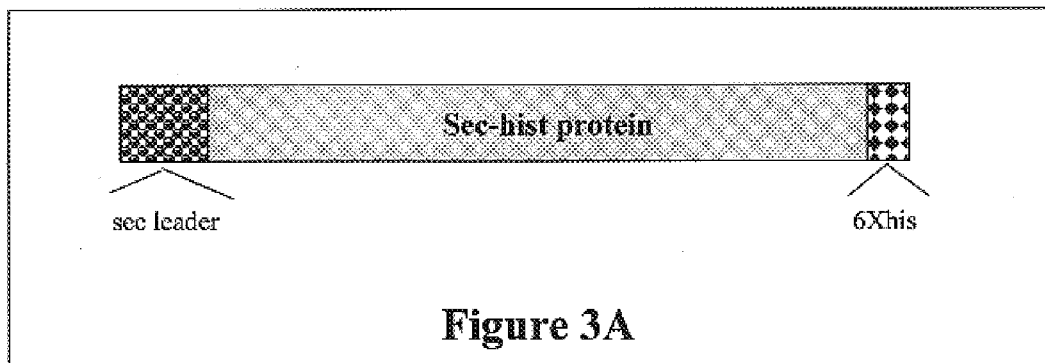
FIGS. 3A & 3B: Schematic representation of sec-hist secretion proteins for screening of structurally altered antigenic polypeptides and the sec-hist expression cassette (SEQ ID NO:17). Panel A: Schematic representation of sec-hist protein; Panel B: Sequence of sec-hist expression cassette. In Panel B, the italic bold sequence represents a HindIll site for subcloning; the double underlined sequence on the 5' end represents leader sequence from the human IL-2; the underlined sequence on the 3' end represents the poly histidine sequence followed by 2 termination codons; sequence in capital letters represents sequence from the polylinker region of pUC18; the polylinker contains the following restriction enzymes for cloning cDNAs: SacI-SacII-NotI-XbaI-SpeI-BamHI-SmaI-PstI-EcoRI.
Figure 4:
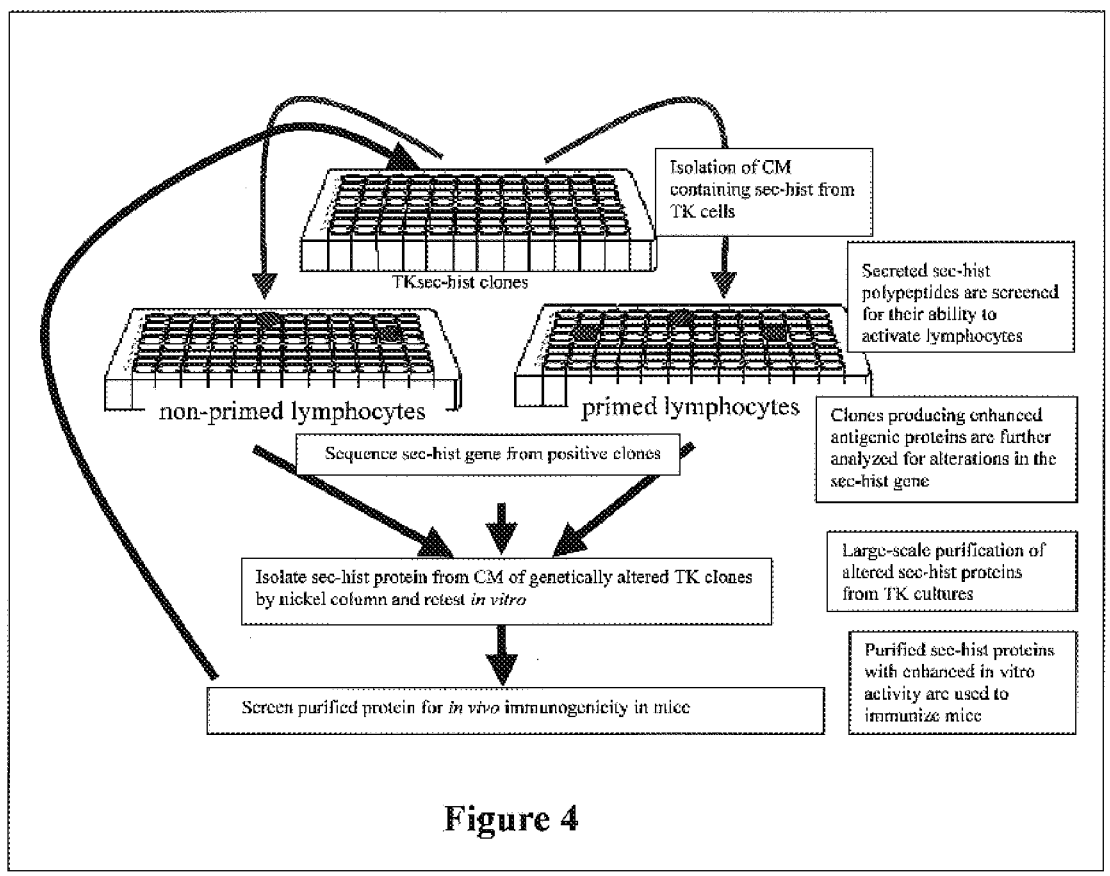
FIG. 4: Schematic diagram for high throughput screening of conditioned medium from TK clones for the identification of antigenic sec-hist polypeptides. Assays employ an in vitro antigenicity test using splenocytes from naive mice (non-primed) and antigen-exposed (primed) mice. Clones exhibiting positive CM are then genetically analyzed to confirm structural alterations within the sec-hist sequence, followed by protein purification and retesting of purified proteins. Purified proteins with the best stimulatory activity are then screened in vivo for immunogenicity. The screening assay can be repeated for several rounds to add additional alterations within the antigen (long arrow).

The inventors have discovered a method for developing hypermutable cells producing therapeutic antigens by taking advantage of the conserved mismatch repair (MMR) process of host cells. Dominant negative alleles of such genes, when introduced into cells or transgenic animals, increase the rate of spontaneous mutations by reducing the effectiveness of DNA repair and thereby render the cells or animals hypermutable. Hypermutable cells or animals can then be utilized to develop new mutations in a gene or genes of interest. Blocking MMR in cells producing antigens (including, but not limited to, mammalian cells, plant cells, yeast cells, and prokaryotic cells) can enhance the rate of mutation within the gene encoding for the antigen that can be screened to identify clones producing structurally altered polypeptides with enhanced antigenicitiy and immunogenicity.

In one aspect of the invention, the methods are useful for the production of antigens that have increased antigenicity and/or immunogenicity. Such antigens may be used as immunogens to elicit immune responses in animals against these antigens.

The antigens may be derived from, for example, pathogenic organisms or cancer cells such that an immune response is directed against the pathogenic organism or cancer cell and exerts an effect on the organism or cancer cell. The effect may be, for example, to prevent, inhibit or terminate the growth of the pathogenic organism or cancer cell when an immunogenic amount of the antigen is administered to an animal.

The pathogenic organisms from which antigens may be derived include bacteria, fungi, parasitic protozoa, helminths, and viruses. Non-limiting examples include species of the following genera: Staphylococcus, Streptococcus, Bacillus, Bordetella, Clostridium, Escherichia, Haemophilus, Helicobacter, Klebsiella, Listeria, Salmonella, Vibrio, Yersinia, Neisseria, Treponema, Borrelia, Corynebacterium, Mycobacterium, Mycoplasma, Chlamydia, Acremonium, Aspergillus, Blastomyces, Candida, Acanthamoeba, Ascaris, Babesia, Cryptosporidium, Echinococcus, Entamoeba, Giardia, Necator, Ancylostoma, Unicinaria, Leishmania, Onchocerca, Plasmodium, Schistosoma, Strongyloides, Taenia, Toxoplasma, Trichinella, Trichomonas, Trichuris, Trypanosoma, Dirofilaria, Brugia, Wuchereria, and Eimeria. Non-limiting examples of viruses include adenovirus, arborviruses, coronavirus, cytomegalovirus, enteroviruses, Epstein-Barr virus, hepatitis viruses, herpes viruses, immunodeficiency viruses (e.g., HIV, FIV SIV), papilloma viruses, T-cell leukemia viruses, influenza viruses, mumps viruses, parainfluenzae viruses, parvoviruses, poxviruses, Rabies virus, respiratory syncytial virus, rhinoviruses, rotaviruses, Rubella viruses, and varicella-zoster viruses.

The antigens derived from the pathogenic organisms, for example, may be antigens known to elicit an immune response, for which an enhanced immune response is desired, or the antigen may be one that is known to generate a weak response for which an enhanced response is desired. It is also possible that some antigens that did not previously elicit an immune response will become antigenic as a result of the methods of the invention and the phenomenon of hypermutability of cells which contain dominant negative alleles of mismatch repair genes.

The antigens produced by the method of the invention are novel immunogens that may be administered in an appropriate pharmaceutical carrier, such as an adjuvant, for administration to animals as a vaccine. The antigens of the invention may be administered to animals in immunogenic amounts such that an antibody and/or a cell-mediated immune response is elicited. The administration of the antigens of the invention may be administered as a single dose, or, preferably as a plurality of doses to effect a boosted immune response. The route of administration may be any accepted route of immunization including, for example, oral, intrmuscular, intrperitoneal, subcutaneous, intradermal, intranasal, or transdermal.

Doses for humans can readily be extrapolated from animal studies as taught by Katocs et al., Chapter 27 of REMINGTON'S PHARMACEUTICAL SCIENCES, 18$^{th}$ Edition, Gennaro (Ed.) Mack Publishing Co., Easton, Pa., 1990. Immunogenic dosages can be adjusted by one skilled in the art, and may vary depending on several factors, including the age, health, physical condition, weight, type and extent of the disease or disorder of the recipient, frequency of treatment, the nature of concurrent therapy, if required, and the nature and scope of the desired effect(s) (Nies et al., Chapter 3, GOODMAN & GILMAN'S THE PHARMACOLOGICAL BASIS OF THERAPEUTICS, 9th Ed., Hardman et al., Eds., McGraw-Hill, New York, N.Y., 1996). Typically, an immunogenic amount of the antigens of the invention will be in the range of about 5 to about 100 g.

The antigens of the present invention may be administered as single antigens or may be administered as combinations of antigens. As a non-limiting example, the antigen combinations may be antigens of the same pathogenic organism, or may be antigens of different pathogenic organisms, such that immune responses are elicited to more than one pathogenic organism.

The antigens of the present invention are hypermutated by the methods of the invention which take advantage of the mismatch repair system. The process of MMR, also called mismatch proofreading, is carried out by protein complexes in cells ranging from bacteria to mammalian cells. A MMR gene is a gene that encodes for one of the proteins of such a mismatch repair complex. Although not wanting to be bound by any particular theory of mechanism of action, a MMR complex is believed to detect distortions of the DNA helix resulting from non-complementary pairing of nucleotide bases. The non-complementary base on the newer DNA strand is excised, and the excised base is replaced with the appropriate base, which is complementary to the older DNA strand. In this way, cells eliminate many mutations that occur as a result of mistakes in DNA replication.

Dominant negative alleies cause a MMR defective phenotype even in the presence of a wild-type allele in the same cell. An example of a dominant negative allele of a MMR gene is the human gene hPMS2-134, which carries a truncating mutation at codon 134. The mutation causes the product of this gene to abnormally terminate at the position of the 134th amino acid, resulting in a shortened polypeptide containing the N-terminal 133 amino acids. Such a mutation causes an increase in the rate of mutations, which accumulate in cells after DNA replication. Expression of a dominant negative allele of a mismatch repair gene results in impairment of mismatch repair activity, even in the presence of the wild-type allele. Any allele that produces such effect can be used in this invention.

Dominant negative alleles of a MMR gene can be obtained from the cells of humans, animals, yeast, bacteria, or other organisms (Prolla T. A. et al. (1994) *Science* 264:1091–1093; Strand M. et al. (1993) *Nature* 365:274–276; Su, S. S. et al. (1988) *J. Biol. Chem.* 263:6829–6835). Such alleles can be identified by screening cells for defective MMR activity. Cells from animals or humans with cancer can be screened for defective mismatch repair. Cells from colon cancer patients may be particularly useful. Genomic DNA, cDNA, or mRNA from any cell encoding a MMR protein can be analyzed for variations from the wild type sequence. Dominant negative alleles of a MMR gene can also be created artificially, for example, by producing variants of the hPMS2-134 allele or other MMR genes. Various techniques of site-directed mutagenesis can be used. The suitability of such alleles, whether natural or artificial, for use in generating hypermutable cells or animals can be evaluated by testing the mismatch repair activity caused by the allele in the presence of one or more wild-type alleles, to determine if it is a dominant negative allele.

A cell or an animal into which a dominant negative allele of a mismatch repair gene has been introduced will become hypermutable. This means that the spontaneous mutation rate of such cells or animals is elevated compared to cells or animals without such alleles. The degree of elevation of the spontaneous mutation rate can be at least 2-fold, 5-fold, 10-fold, 20-fold, 50-fold, 100-fold, 200-fold, 500-fold, or 1000-fold that of the normal cell or animal. The use of chemical mutagens such as but limited to methane sulfonate, dimethyl sulfonate, O6-methyl benzadine, MNU, ENU, etc. can be used in MMR defective cells to increase the rates an additional 10 to 100 fold that of the MMR deficiency itself.

According to one aspect of the invention, a polynucleotide encoding for a dominant negative form of a MMR protein is introduced into a cell. The gene can be any dominant negative allele encoding a protein, which is part of a MMR complex, for example, PMS2, PMS1, MLH1, or MSH2. The dominant negative allele can be naturally occurring or made in the laboratory. The polynucleotide can be in the form of genomic DNA, cDNA, RNA, or a chemically synthesized polynucleotide.

The polynucleotide can be cloned into an expression vector containing a constitutively active promoter segment [such as but not limited to CMV, SV40, Elongation Factor (EF) or LTR sequences] or to inducible promoter sequences such as the steroid inducible pIND vector (InVitrogen), tetracycline, or MMTV, where the expression of the dominant negative MMR gene can be regulated. The polynucleotide can be introduced into the cell by transfection.

According to another aspect of the invention, a gene, a set of genes or a chimeric gene encoding for whole or parts of a therapeutic antigen can be transfected into MMR deficient cell hosts, the cell is grown and screened for clones containing genetically altered genes encoding for antigens with new biochemical features including but not limited to increased antigenicity. MMR defective cells may be of human, primates, mammals, rodent, plant, yeast or of the prokaryotic kingdom.

Transfection is any process whereby a polynucleotide is introduced into a cell. The process of transfection can be carried out in a living animal, e.g., using a vector for gene therapy, or it can be carried out in vitro, e.g., using a suspension of one or more isolated cells in culture. The cell can be any type of eukaryotic cell, including, for example, cells isolated from humans or other primates, mammals or other vertebrates, invertebrates, and single celled organisms such as protozoa, yeast, or bacteria.

In general, transfection will be carried out using a suspension of cells, or a single cell, but other methods can also be applied as long as a sufficient fraction of the treated cells or tissue incorporates the polynucleotide so as to allow transfected cells to be grown and utilized. The protein product of the polynucleotide may be transiently or stably expressed in the cell. Techniques for transfection are well known. Available techniques for introducing polynucleotides include but are not limited to electroporation, transduction, cell fusion, the use of calcium chloride, and packaging of the polynucleotide together with lipid for fusion with the cells of interest. Once a cell has been transfected with the dominant negative MMR gene, the cell can be grown and reproduced in culture. If the transfection is stable, such that the gene is expressed at a consistent level for many cell generations, then a cell line results.

An isolated cell is a cell obtained from a tissue of humans or animals by mechanically separating out individual cells and transferring them to a suitable cell culture medium, either with or without pretreatment of the tissue with enzymes, e.g., collagenase or trypsin. Such isolated cells are typically cultured in the absence of other types of cells. Cells selected for the introduction of a dominant negative allele of a mismatch repair gene may be derived from a eukaryotic organism in the form of a primary cell culture or an immortalized cell line, or may be derived from suspensions of single-celled organisms.

A polynucleotide encoding for a dominant negative form of a MMR protein can be introduced into the genome of an animal by producing a transgenic animal. The animal can be any species for which suitable techniques are available to produce transgenic animals. For example, transgenic animals can be prepared from domestic livestock, e.g., bovine, swine, sheep, goats, horses, etc.; from animals used for the production of recombinant proteins, e.g., bovine, swine, or goats that express a recombinant polypeptide in their milk; or experimental animals for research or product testing, e.g., mice, rats, guinea pigs, hamsters, rabbits, etc. Cell lines that are determined to be MMR defective can then be used as a source for producing genetically altered genes encoding for therapeutic antigens in vitro by introducing whole, intact genes and/or chimeric genes encoding for a therapeutic antigen(s) into MMR defective cells from any tissue of the MMR defective animal.

Once a transfected cell line or a colony of transgenic animals has been produced, it can be used to generate new mutations in one or more gene(s) of interest. A gene of interest can be any gene naturally possessed by the cell line or transgenic animal or introduced into the cell line or transgenic animal. An advantage of using such cells or animals to induce mutations is that the cell or animal need not be exposed to mutagenic chemicals or radiation, which may have secondary harmful effects, both on the object of the exposure and on the workers. However, chemical mutagens may be used in combination with MMR deficiency, which renders such mutagens less toxic due to an undetermined mechanism. Hypermutable animals can then be bred and selected for those producing genetically variable cells that may be isolated and cloned to identify new cell lines that are useful for producing structurally altered polypeptides. Once an altered polypeptide is identified, the dominant negative MMR gene allele can be removed by directly knocking out the allele by technologies used by those skilled in the art or by breeding to mates lacking the dominant negative allele to select for offspring with a desired trait and a stable genome. Another alternative is to use a CRE-LOX expression system, whereby the dominant negative allele is spliced from the animal genome once an animal containing a genetically diverse protein profile has been established. Yet another alternative is the use of inducible vectors such as the steroid induced pIND (InVitrogen) or pMAM (Clonetech) vectors which express exogenous genes in the presence of corticosteroids.

Mutations can be detected by analyzing for alterations in the genotype of the cells or animals, for example by examining the sequence of genomic DNA, cDNA, messenger RNA, or amino acids associated with the gene of interest. Mutations can also be detected by screening for the production of antigenicity. A mutant polypeptide can be detected by identifying alterations in electrophoretic mobility, spectroscopic properties, or other physical or structural characteristics of a protein encoded by a mutant gene. One can also screen for altered function of the protein in situ, in isolated form, or in model systems. One can screen for alteration of any property of the cell or animal associated with the function of the gene of interest, such as but not limited to antigenicity.

According to another aspect of the invention, a high throughput mammalian cell-based assay is presented. A MMR defective cell line is transfected with a secretion cassette containing a leader sequence for secretion at the N-terminus fused to the target antigen. Cells are grown and clones are plated by limiting dilution into microtitre plates and conditioned medium are screened for antigenic peptides. The advantage of such an approach is that the antigen is more similar to the natural polypeptide than it would be if produced by bacterial, yeast or baculovirus systems which tend to cause misfolding and/or distorted post-translational modifications.

Examples of mismatch repair proteins and nucleic acid sequences include the following:

PMS2 (mouse) (SEQ ID NO:5)

| | | | | | |
|---|---|---|---|---|---|
| MEQTEGVSTE | CAKAIKPIDG | KSVHQICSGQ | VILSLSTAVK | ELIENSVDAG | ATTIDLRLKD   60 |
| YGVDLIEVSD | NGCGVEEENF | EGLALKHHTS | KIQEFADLTQ | VETFGFRGEA | LSSLCALSDV  120 |
| TISTCHGSAS | VGTRLVFDHN | GKITQKTPYP | RPKGTTVSVQ | HLFYTLPVRY | KEFQRNIKKE  180 |
| YSKMVQVLQA | YCIISAGVRV | SCTNQLGQGK | RHAVVCTSGT | SGMKENIGSV | FGQKQLQSLI  240 |
| PFVQLPPSDA | VCEEYGLSTS | GRHKTFSTFR | ASFHSARTAP | GGVQQTGSFS | SSIRGPVTQQ  300 |
| RSLSLSMRFY | HMYNRHQYPF | VVLNVSVDSE | CVDINVTPDK | RQILLQEEKL | LLAVLKTSLI  360 |
| GMFDSDANKL | NVNQQPLLDV | EGNLVKLHTA | ELEKPVPGKQ | DNSPSLKSTA | DEKRVASISR  420 |
| LREAFSLHPT | KEIKSRGPET | AELTRSFPSE | KRGVLSSYPS | DVISYRGLRG | SQDKLVSPTD  480 |
| SPGDCMDREK | IEKDSGLSST | SAGSEEEFST | PEVASSFSSD | YNVSSLEDRP | SQETINCGDL  540 |
| DCRPPGTGQS | LKPEDHGYQC | KALPLARLSP | TNAKRFKTEE | RPSNVNISQR | LPGPQSTSAA  600 |
| EVDVAIKMNK | RIVLLEFSLS | SLAKRMKQLQ | HLKAQNKHEL | SYRKFRAKIC | PGENQAAEDE  660 |
| LRKEISKSMF | AEMEILGQFN | LGFIVTKLKE | DLFLVDQHAA | DEKYNFEMLQ | QHTVLQAQRL  720 |
| ITPQTLNLTA | VNEAVLIENL | EIFRKNGFDF | VIDEDAPVTE | RAKLISLPTS | KNWTFGPQDI  780 |
| DELIFMLSDS | PGVMCRPSRV | RQMFASRACR | KSVMIGTALN | ASEMKKLITH | MGEMDHPWNC  840 |
| PHGRPTMRHV | ANLDVISQN | | | |             859 |

PMS2 (mouse CDNA) (SEQ ID NO:6)

| | | | | | |
|---|---|---|---|---|---|
| gaattccggt | gaaggtcctg | aagaatttcc | agattcctga | gtatcattgg | aggagacaga   60 |
| taacctgtcg | tcaggtaacg | atggtgtata | tgcaacagaa | atgggtgttc | ctggagacgc  120 |
| gtcttttccc | gagagcggca | ccgcaactct | cccgcggtga | ctgtgactgg | aggagtcctg  180 |
| catccatgga | gcaaaccgaa | ggcgtgagta | cagaatgtgc | taaggccatc | aagcctattg  240 |
| atgggaagtc | agtccatcaa | atttgttctg | ggcaggtgat | actcagttta | agcaccgctg  300 |
| tgaaggagtt | gatagaaaat | agtgtagatg | ctggtgctac | tactattgat | ctaaggctta  360 |
| aagactatgg | ggtggacctc | attgaagttt | cagacaatgg | atgtggggta | gaagaagaaa  420 |
| actttgaagg | tctagctctg | aaacatcaca | catctaagat | tcaagagttt | gccgacctca  480 |
| cgcaggttga | aactttcggc | tttcggggg | aagctctgag | ctctctgtgt | gcactaagtg  540 |
| atgtcactat | atctacctgc | cacgggtctg | caagcgttgg | gactcgactg | gtgtttgacc  600 |
| ataatgggaa | aatcacccag | aaaactccct | acccccgacc | taaggaacc | acagtcagtg  660 |
| tgcagcactt | attttataca | ctacccgtgc | gttacaaaga | gtttcagagg | aacattaaaa  720 |
| aggagtattc | caaaatggtg | caggtcttac | aggcgtactg | tatcatctca | gcaggcgtcc  780 |
| gtgtaagctg | cactaatcag | ctcggacagg | ggaagcggca | cgctgtggtg | tgcacaagcg  840 |
| gcacgtctgg | catgaaggaa | aatatcgggt | ctgtgtttgg | ccagaagcag | ttgcaaagcc  900 |
| tcattccttt | tgttcagctg | cccctagtg | acgctgtgtg | tgaagagtac | ggcctgagca  960 |
| cttcaggacg | ccacaaaacc | ttttctacgt | ttcgggcttc | atttcacagt | gcacgcacgg 1020 |
| cgccgggagg | agtgcaacag | acaggcagtt | tttcttcatc | aatcagaggc | cctgtgaccc 1080 |
| agcaaaggtc | tctaagcttg | tcaatgaggt | tttatcacat | gtataaccgg | catcagtacc 1140 |
| catttgtcgt | ccttaacgtt | tccgttgact | cagaatgtgt | ggatattaat | gtaactccag 1200 |
| ataaaaggca | aattctacta | caagaagaga | agctattgct | ggccgtttta | aagacctcct 1260 |

-continued

```
tgataggaat gtttgacagt gatgcaaaca agcttaatgt caaccagcag ccactgctag   1320
atgttgaagg taacttagta aagctgcata ctgcagaact agaaaagcct gtgccaggaa   1380
agcaagataa ctctccttca ctgaagagca cagcagacga gaaaagggta gcatccatct   1440
ccaggctgag agaggccttt tctcttcatc ctactaaaga gatcaagtct aggggtccaa   1500
agactgctga actgacacgg agttttccaa gtgagaaaag gggcgtgtta tcctcttatc   1560
cttcagacgt catctcttac agaggcctcc gtggctcgca ggacaaattg gtgagtccca   1620
cggacagccc tggtgactgt atggacagag agaaaataga aaaagactca gggctcagca   1680
gcacctcagc tggctctgag gaagagttca gcaccccaga agtggccagt agctttagca   1740
gtgactataa cgtgagctcc ctagaagaca gaccttctca ggaaaccata aactgtggtg   1800
acctggactg ccgtcctcca ggtacaggac agtccttgaa gccagaagac catggatatc   1860
aatgcaaagc tctacctcta gctcgtctgt cacccacaaa tgccaagcgc ttcaagacag   1920
aggaaagacc ctcaaatgtc aacatttctc aaagattgcc tggtcctcag agcacctcag   1980
cagctgaggt cgatgtagcc ataaaaatga ataagagaat cgtgctcctc gagttctctc   2040
tgagttctct agctaagcga atgaagcagt tacagcacct aaaggcgcag aacaaacatg   2100
aactgagtta cagaaaattt agggccaaga tttgccctgg agaaaaccaa gcagcagaag   2160
atgaactcag aaaagagatt agtaaatcga tgtttgcaga gatggagatc ttgggtcagt   2220
ttaacctggg atttatagta accaaactga agaggaccct cttcctggtg gaccagcatg   2280
ctgcggatga gaagtacaac tttgagatgc tgcagcagca cacggtgctc caggcgcaga   2340
ggctcatcac accccagact ctgaacttaa ctgctgtcaa tgaagctgta ctgatagaaa   2400
atctggaaat attcagaaag aatggctttg actttgtcat tgatgaggat gctccagtca   2460
ctgaaagggc taaattgatt tccttaccaa ctagtaaaaa ctggaccttt ggaccccaag   2520
atatagatga actgatcttt atgttaagtg acagccctgg ggtcatgtgc cggccctcac   2580
gagtcagaca gatgtttgct tccagagcct gtcggaagtc agtgatgatt ggaacggcgc   2640
tcaatgcgag cgagatgaag aagctcatca cccacatggg tgagatggac cacccctgga   2700
actgcccca cggcaggcca accatgaggc acgttgccaa tctggatgtc atctctcaga   2760
actgacacac cccttgtagc atagagtttta ttacagattg ttcggtttgc aaagagaagg   2820
tttttaagtaa tctgattatc gttgtacaaa aattagcatg ctgctttaat gtactggatc   2880
catttaaaag cagtgttaag gcaggcatga tggagtgttc ctctagctca gctacttggg   2940
tgatccggtg ggagctcatg tgagcccagg actttgagac cactccgagc cacattcatg   3000
agactcaatt caaggacaaa aaaaaaaaga tattttttgaa gcctttttaaa aaaaaa     3056
```

PMS2 (human) (SEQ ID NO:7)

```
MERAESSSTE PAKAIKPIDR KSVHQICSGQ VVLSLSTAVK ELVENSLDAG ATNIDLKLKD    60
YGVDLIEVSD NGCGVEEENF EGLTLKHHTS KIQEFADLTQ VETFGFRGEA LSSLCALSDV   120
TISTCHASAK VGTRLMFDHN GKIIQKTPYP RPRGTTVSVQ QLFSTLPVRH KEFQRNIKKE   180
YAKMVQVLHA YCIISAGIRV SCTNQLGQGK RQPVVCTGGS PSIKENIGSV FGQKQLQSLI   240
PFVQLPPSDS VCEEYGLSCS DALHNLFYIS GFISQCTHGV GRSSTDRQFF FINRRPCDPA   300
KVCRLVNEVY HMYNRHQYPF VVLNISVDSE CVDINVTPDK RQILLQEEKL LLAVLKTSLI   360
GMFDSDVNKL NVSQQPLLDV EGNLIKMHAA DLEKPMVEKQ DQSPSLRTGE EKKDVSISRL   420
REAFSLRHTT ENKPHSPKTP EPRRSPLGQK RGMLSSSTSG AISDKGVLRP QKEAVSSSHG   480
PSDPTDRAEV EKDSGHGSTS VDSEGFSIPD TGSHCSSEYA ASSPGDRGSQ EHVDSQEKAP   540
```

-continued

```
ETDDSFSDVD CHSNQEDTGC KFRVLPQPTN LATPNTKRFK KEEILSSSDI CQKLVNTQDM    600
SASQVDVAVK INKKVVPLDF SMSSLAKRIK QLHHEAQQSE GEQNYRKFPA KICPGENQAA    660
EDELRKEISK TMFAEMEIIG QFNLGFIITK LNEDIFIVDQ HATDEKYNFE MLQQHTVLQG    720
QRLIAPQTLN LTAVNEAVLI ENLEIFRKNG FDFVIDENAP VTERAKLISL PTSKNWTFGP    780
QDVDELIFML SDSPGVMCRP SRVKQMFASR ACRKSVMIGT ALNTSEMKKL ITHMGEMDHP    840
WNCPHGRPTM RHIANLGVIS QN                                            862
```

PMS2 (human cDNA) (SEQ ID NO:8)

```
cgaggcggat cgggtgttgc atccatggag cgagctgaga gctcgagtac agaacctgct     60
aaggccatca aacctattga tcggaagtca gtccatcaga tttgctctgg caggtggta    120
ctgagtctaa gcactgcggt aaaggagtta gtagaaaaca gtctggatgc tggtgccact    180
aatattgatc taaagcttaa ggactatgga gtggatctta ttgaagtttc agacaatgga    240
tgtggggtag aagaagaaaa cttcgaaggc ttaactctga acatcacac atctaagatt    300
caagagtttg ccgacctaac tcaggttgaa acttttggct tcgggggga agctctgagc    360
tcactttgtg cactgagcga tgtcaccatt tctacctgcc acgcatcgg gaaggttgga    420
actcgactga tgtttgatca caatgggaaa attatccaga aaccccta ccccgcccc    480
agagggacca cagtcagcgt gcagcagtta ttttccacac tacctgtgcg ccataaggaa    540
tttcaaagga atattaagaa ggagtatgcc aaaatggtcc aggtcttaca tgcatactgt    600
atcatttcag caggcatccg tgtaagttgc accaatcagc ttggacaagg aaaacgacag    660
cctgtggtat gcacaggtgg aagccccagc ataaggaaa atatcggctc tgtgtttggg    720
cagaagcagt tgcaaagcct cattcctttt gttcagctgc ccctagtga ctccgtgtgt    780
gaagagtacg gtttgagctg ttcggatgct ctgcataatc tttttttacat ctcaggtttc    840
atttcacaat gcacgcatgg agttggaagg agttcaacag acagacagtt tttctttatc    900
aaccggcggc cttgtgaccc agcaaaggtc tgcagactcg tgaatgaggt ctaccacatg    960
tataatcgac accagtatcc atttgttgtt cttaacattt ctgttgattc agaatgcgtt   1020
gatatcaatg ttactccaga taaaaggcaa attttgctac aagaggaaaa gcttttgttg   1080
gcagttttaa agacctcttt gataggaatg tttgatagtg atgtcaacaa gctaaatgtc   1140
agtcagcagc cactgctgga tgttgaaggt aacttaataa aaatgcatgc agcggatttg   1200
gaaaagccca tggtagaaaa gcaggatcaa tccccttcat taaggactgg agaagaaaaa   1260
aaagacgtgt ccatttccag actgcgagag gcctttttctc ttcgtcacac aacagagaac   1320
aagcctcaca gcccaaagac tccagaacca gaaggagcc ctctaggaca gaaaaggggt   1380
atgctgtctt ctagcacttc aggtgccatc tctgacaaag cgtcctgag acctcagaaa   1440
gaggcagtga gttccagtca cggacccagt gacctacgg acagagcgga ggtggagaag   1500
gactcggggc acgcagcac ttccgtggat tctgagggt cagcatccc agacacgggc   1560
agtcactgca gcagcgagta tgcggccagc tccccagggg acaggggctc gcaggaacat   1620
gtggactctc aggagaaagc gcctgaaact gacgactctt tttcagatgt ggactgccat   1680
tcaaaccagg aagataccgg atgtaaattt cgagttttgc ctcagccaac taatctcgca   1740
accccaaaca caaagcgttt taaaaaagaa gaaattcttt ccagttctga catttgtcaa   1800
aagttagtaa atactcagga catgtcagcc tctcaggttg atgtagctgt gaaaattaat   1860
aagaaagttg tgcccctgga ctttttctatg agttctttag ctaaacgaat aaagcagtta   1920
catcatgaag cacagcaaag tgaaggggaa cagaattaca ggaagtttag ggcaaagatt   1980
```

-continued

```
tgtcctggag aaaatcaagc agccgaagat gaactaagaa aagagataag taaaacgatg    2040
tttgcagaaa tggaaatcat tggtcagttt aacctgggat ttataataac caaactgaat    2100
gaggatatct tcatagtgga ccagcatgcc acggacgaga agtataactt cgagatgctg    2160
cagcagcaca ccgtgctcca ggggcagagg ctcatagcac ctcagactct caacttaact    2220
gctgttaatg aagctgttct gatagaaaat ctggaaatat ttagaaagaa tggctttgat    2280
tttgttatcg atgaaaatgc tccagtcact gaaagggcta aactgatttc cttgccaact    2340
agtaaaaact ggaccttcgg accccaggac gtcgatgaac tgatcttcat gctgagcgac    2400
agccctgggg tcatgtgccg gccttcccga gtcaagcaga tgtttgcctc cagagcctgc    2460
cggaagtcgg tgatgattgg gactgctctt aacacaagcg agatgaagaa actgatcacc    2520
cacatggggg agatggacca ccctggaac tgtccccatg aaggccaac catgagacac    2580 atcgccaacc tgggtgtcat ttctcagaac tgaccgtagt cactgtatgg aataattggt    2640
tttatcgcag atttttatgt tttgaaagac agagtcttca ctaaccttt ttgttttaaa    2700 atgaaacctg ctacttaaaa aaaatacaca tcacacccat ttaaaagtga tcttgagaac    2760
cttttcaaac c                                                        2771
```

PMS1 (human) (SEQ ID NO:9)

```
MKQLPAATVR LLSSSQIITS VVSVVKELIE NSLDAGATSV DVKLENYGFD KIEVRDNGEG     60

IKAVDAPVMA MKYYTSKINS HEDLENLTTY GFRGEALGSI CCIAEVLITT RTAADNFSTQ    120

YVLDGSGHIL SQKPSHLGQG TTVTALRLFK NLPVRKQFYS TAKKCKDEIK KIQDLLMSFG    180

ILKPDLRIVF VHNKAVIWQK SRVSDHKMAL MSVLGTAVMN NMESFQYHSE ESQIYLSGFL    240

PKCDADHSFT SLSTPERSFI FINSRPVHQK DILKLIRHHY NLKCLKESTR LYPVFFLKID    300

VPTADVDVNL TPDKSQVLLQ NKESVLIALE NLMTTCYGPL PSTNSYENNK TDVSAADIVL    360

SKTAETDVLF NKVESSGKNY SNVDTSVIPF QNDMHNDESG KNTDDCLNHQ ISIGDFGYGH    420

CSSEISNIDK NTKNAFQDIS MSNVSWENSQ TEYSKTCFIS SVKHTQSENG NKDHIDESGE    480

NEEEAGLENS SEISADEWSR GNILKNSVGE NIEPVKILVP EKSLPCKVSN NNYPIPEQMN    540

LNEDSCNKKS NVIDNKSGKV TAYDLLSNRV IKKPMSASAL FVQDHRPQFL IENPKTSLED    600

ATLQIEELWK TLSEEEKLKY EEKATKDLER YNSQMKRAIE QESQMSLKDG RKKIKPTSAW    660

NLAQKHKLKT SLSNQPKLDE LLQSQIEKRR SQNIKMVQIP FSMKNLKINF KKQNKVDLEE    720

KDEPCLIHNL RFPDAWLMTS KTEVMLLNPY RVEEALLFKR LLENHKLPAE PLEKPIMLTE    780

SLFNGSHYLD VLYKMTADDQ RYSGSTYLSD PRLTANGFKI KLIPGVSITE NYLEIEGMAN    840

CLPFYGVADL KEILNAILNR NAKEVYECRP RKVISYLEGE AVRLSRQLPM YLSKEDIQDI    900

IYRMKHQFGN EIKECVHGRP FFHHLTYLPE TT                                  932
```

PMS1 (human) (SEQ ID NO:10)

```
ggcacgagtg gctgcttgcg gctagtggat ggtaattgcc tgcctcgcgc tagcagcaag     60
ctgctctgtt aaaagcgaaa atgaaacaat gccctgcggc aacagttcga ctcctttcaa    120
gttctcagat catcacttcg gtggtcagtg ttgtaaaaga gcttattgaa aactccttgg    180
atgctggtgc cacaagcgta gatgttaaac tggagaacta tggatttgat aaaattgagg    240
tgcgagataa cggggagggt atcaaggctg ttgatgcacc tgtaatggca atgaagtact    300
acacctcaaa aataaatagt catgaagatc ttgaaaattt gacaacttac ggttttcgtg    360
gagaagcctt gggtcaatt tgttgtatag ctgaggtttt aattacaaca agaacggctg    420
ctgataattt tagcacccag tatgttttag atggcagtgg ccacatactt tctcagaaac    480
```

-continued

```
cttcacatct tggtcaaggt acaactgtaa ctgctttaag attatttaag aatctacctg      540
taagaaagca gttttactca actgcaaaaa aatgtaaaga tgaaataaaa aagatccaag      600
atctcctcat gagctttggt atccttaaac ctgacttaag gattgtcttt gtacataaca      660
aggcagttat ttggcagaaa agcagagtat cagatcacaa gatggctctc atgtcagttc      720
tggggactgc tgttatgaac aatatggaat cctttcagta ccactctgaa gaatctcaga      780
tttatctcag tggatttctt ccaaagtgtg atgcagacca ctctttcact agtctttcaa      840
caccagaaag aagtttcatc ttcataaaca gtcgaccagt acatcaaaaa gatatcttaa      900
agttaatccg acatcattac aatctgaaat gcctaaagga atctactcgt ttgtatcctg      960
ttttctttct gaaaatcgat gttcctacag ctgatgttga tgtaaattta acaccagata     1020
aaagccaagt attattacaa aataaggaat ctgttttaat tgctcttgaa atctgatga     1080 cgacttgtta tggaccatta cctagtacaa attcttatga aataataaa acagatgttt     1140 ccgcagctga catcgttctt agtaaaacag cagaaacaga tgtgcttttt aataaagtgg     1200
aatcatctgg aaagaattat tcaaatgttg atacttcagt cattccattc caaaatgata     1260
tgcataatga tgaatctgga aaaaacactg atgattgttt aaatcaccag ataagtattg     1320
gtgactttgg ttatggtcat t9tagtagtg aaatttctaa cattgataaa aacactaaga     1380
atgcatttca ggacatttca atgagtaatg tatcatggga gaactctcag acggaatata     1440
gtaaaacttg ttttataagt tccgttaagc acacccagtc agaaaatggc aataaagacc     1500
atatagatga gagtggggaa aatgaggaag aagcaggtct tgaaaactct tcggaaattt     1560
ctgcagatga gtggagcagg ggaaatatac ttaaaaattc agtgggagag aatattgaac     1620
ctgtgaaaat tttagtgcct gaaaaaagtt taccatgtaa agtaagtaat aataattatc     1680
caatccctga acaaatgaat cttaatgaag attcatgtaa caaaaaatca aatgtaatag     1740
ataataaatc tggaaaagtt acagcttatg atttacttag caatcgagta atcaagaaac     1800
ccatgtcagc aagtgctctt tttgttcaag atcatcgtcc tcagtttctc atagaaaatc     1860
ctaagactag tttagaggat gcaacactac aaattgaaga actgtggaag acattgagtg     1920
aagaggaaaa actgaaatat gaagagaagg ctactaaaga cttggaacga tacaatagtc     1980
aaatgaagag agccattgaa caggagtcac aaatgtcact aaaagatggc agaaaaaaga     2040
taaaacccac cagcgcatgg aatttggccc agaagcacaa gttaaaaacc tcattatcta     2100
atcaaccaaa acttgatgaa ctccttcagt cccaaattga aaaagaagg agtcaaaata     2160 ttaaaatggt acagatcccc ttttctatga aaaacttaaa aataaatttt aagaaacaaa     2220
acaaagttga cttagaagag aaggatgaac cttgcttgat ccacaatctc aggtttcctg     2280
atgcatggct aatgacatcc aaaacagagg taatgttatt aaatccatat agagtagaag     2340
aagccctgct atttaaaaga cttcttgaga atcataaact tcctgcagag ccactggaaa     2400
agccaattat gttaacagag agtctttta atggatctca ttatttagac gttttatata     2460
aaatgacagc agatgaccaa agatacagtg gatcaactta cctgtctgat cctcgtcta     2520 cagcgaatgg tttcaagata aaattgatac caggagtttc aattactgaa aattacttgg     2580
aaatagaagg aatggctaat tgtctcccat tctatggagt agcagattta aaagaaattc     2640
ttaatgctat attaaacaga aatgcaaagg aagtttatga atgtagacct cgcaaagtga     2700
taagttattt agagggagaa gcagtgcgtc tatccagaca attacccatg tacttatcaa     2760
aagaggacat ccaagacatt atctacagaa tgaagcacca gttggaaat gaaattaaag     2820 agtgtgttca tggtcgccca tttttttcatc atttaaccta tcttccagaa actacatgat     2880
```

-continued

```
taaatatgtt taagaagatt agttaccatt gaaattggtt ctgtcataaa acagcatgag    2940
tctggtttta aattatcttt gtattatgtg tcacatggtt atttttaaa tgaggattca     3000 ctgacttgtt tttatattga aaaagttcc acgtattgta gaaaacgtaa ataaactaat    3060
aac                                                                  3063
```

MSH2 (human) (SEQ ID NO:11)

```
MAVQPKETLQ LESAAEVGFV RFFQGMPEKP TTTVRLFDRG DFYTARGEDA LLAAREVFKT      60

QGVIKYMGPA GAKNLQSVVL SKMNFESFVK DLLLVRQYRV EVYKNRAGNK ASKENDWYLA    120

YKASPGNLSQ FEDTLFGNND MSASIGVVGV KMSAVDGQRQ VGVGYVDSIQ RKLGLCEFPD    180

NDQFSNLEAL LIQIGPKECV LPGGETAGDM GKLRQIIQRG GILITERKKA DFSTKDIYQD    240

LNRLLKGKKG EQMNSAVLPE MENQVAVSSL SAVIKFLELL SDDSNFGQFE LTTFDFSQYM    300

KLDIAAVRAL NLFQGSVEDT TGSQSLAALL NKCKTPQGQR LVNQWIKQPL MDKNRIEERL    360

NLVEAFVEDA ELRQTLQEDL LRRFPDLNRL AKKFQRQAAN LQDCYRLYQG INQLPNVIQA    420

LEKHEGKHQK LLLAVFVTPL TDLRSDFSKF QEMIETTLDM DQVENREFLV KPSFDPNLSE    480

LREIMNDLEK KMQSTLISAA RDLGLDPGKQ IKLDSSAQFG YYFRVTCKEE KVLRNNKNFS    540

TVDIQKNGVK FTNSKLTSLN EEYTKNKTEY EEAQDAIVKE IVNISSGYVE PMQTLNDVLA    600

QLDAVVSFAH VSNGAPVPYV RPAILEKGQG RIILKASRHA CVEVQDEIAF IPNDVYFEKD    660

KQMFHIITGP NMGGKSTYIR QTGVIVLMAQ IGCFVPCESA EVSIVDCILA RVGAGDSQLK    720

GVSTFMAEML ETASILRSAT KDSLIIIDEL GRGTSTYDGF GLAWAISEYI ATKIGAFCMF    780

ATHFHELTAL ANQIPTVNNL RVTALTTEET LTMLYQVKKG VCDQSFGIHV AELANFPKHV    840

IECAKQKALE LEEFQYIGES QGYDIMEPAA KKCYLEREQG EKIIQEFLSK VKQMPFTEMS    900

EENITIKLKQ LKAEVIAKNN SFVNEIISRI KVTT                                934
```

MSH2 (human cDNA) (SEQ ID NO:12)

```
ggcgggaaac agcttagtgg gtgtggggtc gcgcattttc ttcaaccagg aggtgaggag     60
gtttcgacat ggcggtgcag ccgaaggaga cgctgcagtt ggagagcgcg gccgaggtcg    120
gcttcgtgcg cttctttcag ggcatgccgg agaagccgac caccacagtg cgccttttcg    180
accgggcgga cttctatacg gcgcacggcg aggacgcgct gctggccgcc cgggaggtgt    240
tcaagaccca gggggtgatc aagtacatgg ggccggcagg agcaaagaat ctgcagagtg    300
ttgtgcttag taaaatgaat tttgaatctt ttgtaaaaga tcttcttctg gttcgtcagt    360
atagagttga agtttataag aatagagctg gaaataagga atccaaggag aatgattggt    420
atttggcata taaggcttct cctggcaatc tctctcagtt tgaagacatt ctctttggta    480
acaatgatat gtcagcttcc attggtgttg tgggtgttaa aatgtccgca gttgatggcc    540
agagacaggt tggagttggg tatgtggatt ccatacagag gaaactagga ctgtgtgaat    600
tccctgataa tgatcagttc tccaatcttg aggctctcct catccagatt ggaccaaagg    660
aatgtgtttt acccggagga gagactgctg gagacatggg gaaactgaga cagataattc    720
aaagaggagg aattctgatc acagaaagaa aaaagctga cttttccaca aaagacattt    780
atcaggacct caaccggttg ttgaaaggca aaaagggaga gcagatgaat agtgctgtat    840
tgccagaaat ggagaatcag gttgcagttt catcactgtc tgcggtaatc aagttttag    900 aactcttatc agatgattcc aactttggac agtttgaact gactactttt gacttcagcc    960
agtatatgaa attggatatt gcagcagtca gagcccttaa ccttttttcag ggttctgttg   1020 aagataccac tggctctcag tctctggctg ccttgctgaa taagtgtaaa acccctcaag   1080
```

-continued

```
gacaaagact tgttaaccag tggattaagc agcctctcat ggataagaac agaatagagg    1140
agagattgaa tttagtggaa gcttttgtag aagatgcaga attgaggcag actttacaag    1200
aagatttact tcgtcgattc ccagatctta accgacttgc caagaagttt caaagacaag    1260
cagcaaactt acaagattgt taccgactct atcagggtat aaatcaacta cctaatgtta    1320
tacaggctct ggaaaaacat gaaggaaaac accagaaatt attgttggca gttttttgtga   1380 ctcctcttac tgatcttcgt tctgacttct ccaagtttca ggaaatgata gaaacaactt    1440
tagatatgga tcaggtggaa aaccatgaat tccttgtaaa accttcattt gatcctaatc    1500
tcagtgaatt aagagaaata atgaatgact ggaaaagaa gatgcagtca acattaataa     1560
gtgcagccag atcttggc ttggaccctg caaacagat taaactggat tccagtgcac       1620
agtttggata ttactttcgt gtaacctgta aggaagaaaa agtccttcgt aacaataaaa    1680
actttagtac tgtagatatc cagaagaatg gtgttaaatt taccaacagc aaattgactt   1740 cttaaatga gagtatacc aaaaataaaa cagaatatga agaagcccag gatgccattg      1800
ttaaagaaat tgtcaatatt tcttcaggct atgtagaacc aatgcagaca ctcaatgatg    1860
tgttagctca gctagatgct gttgtcagct ttgctcacgt gtcaaatgga gcacctgttc    1920
catatgtacg accagccatt ttggagaaag gacaaggaag aattatatta aaagcatcca   1980
ggcatgcttg tgttgaagtt caagatgaaa ttgcatttat tcctaatgac gtatactttg    2040
aaaaagataa acagatgttc cacatcatta ctggccccaa tatgggaggt aaatcaacat    2100
atattcgaca aactggggtg atagtactca tggcccaaat tgggtgtttt gtgccatgtg    2160
agtcagcaga agtgtccatt gtggactgca tcttagcccg agtaggggct ggtgacagtc    2220
aattgaaagg agtctccacg ttcatggctg aaatgttgga aactgcttct atcctcaggt    2280
ctgcaaccaa agattcatta taatcatag atgaattggg aagaggaact tctacctacg     2340
atggatttgg gttagcatgg gctatatcag aatacattgc aacaaagatt ggtgcttttt     2400
gcatgtttgc aacccatttt catgaactta ctgccttggc caatcagata ccaactgtta    2460
ataatctaca tgtcacagca ctcaccactg aagagacctt aactatgctt tatcaggtga    2520
agaaaggtgt ctgtgatcaa agttttggga ttcatgttgc agagcttgct aatttcccta    2580
agcatgtaat agagtgtgct aaacagaaag ccctggaact tgaggagttt cagtatattg    2640
gagaatcgca aggatatgat atcatggaac cagcagcaaa gaagtgctat ctggaaagag    2700
agcaaggtga aaaaattatt caggagttcc tgtccaaggt gaaacaaatg ccctttactg    2760
aaatgtcaga gaaaacatc acaataaagt taaacagctc aaaagctgaa gtaatagcaa     2820
agaataatag ctttgtaaat gaatcattt cacgaataaa agttactacg tgaaaaatcc      2880
cagtaatgga atgaaggtaa tattgataag ctattgtctg taatagtttt atattgtttt     2940
atattaaccc tttttccata gtgttaactg tcagtgccca tgggctatca acttaataag    3000
atatttagta atatttact ttgaggacat tttcaaagat ttttattttg aaaaatgaga     3060
gctgtaactg aggactgttt gcaattgaca taggcaataa taagtgatgt gctgaatttt    3120
ataaataaaa tcatgtagtt tgtgg                                           3145
```

MLH1 (human) (SEQ ID NO:13)

```
MSFVAGVIRR LDETVVNRIA AGEVIQRPAN AIKEMIENCL DAKSTSIQVI VKEGGLKLIQ     60

IQDNCTGIRK EDLDIVCERF TTSKLQSFED LASISTYGFR GEALASISHV AHVTITTKTA   120

DGKCAYRASY SDGKLAPPK PCAGNQGTQJ TVEDLFYNIA TRRKALKNPS EEYGKILEVV    180

GRYSVHNAGI SFSVKKQGET VADVRTLPNA STVDNIRSIF GNAVSRELIE IGCEDKTLAF   240
```

-continued

```
KMNGYISNAN YSVKKCIFLL FINHRLVEST SLRKAIETVY AAYLPKNTHP FLYLSLEISP    300
QNVDVNVHPT KHEVHFLREE SILERVQQHI ESKLLGSNSS RMYFTQTLLP GLAGPSGEMV    360
KSTTSLTSSS TSGSSDKVYA HQMVRTDSRE QKLDAFLQPL SKPLSSQPQA IVTEDKTDIS    420
SGRARQQDEE MLELPAPAEV AAKNQSLEGD TTKGTSEMSE KRGPTSSNPR KRHREDSDVE    480
MVEDDSRKEM TAACTPRRRI INLTSVLSLQ EETNEQGREV LREMLHNHSF VGCVNPQWAL    540
AQHQTKLYLL NTTKLSEELF YQILIYDFAN FGVLRLSEPA PLFDLAMLAL DSPESGWTEE    600
DGPKEGLAEY IVEFLKKKAE MLADYFSLEI DEEGNLIGLP LLIDNYVPPL EGLPIFILRL    660
ATEVNWDEEK ECFESLSKEC AMFYSIRKQY ISEESTLSGQ QSEVPGSIPN SWKWTVEHIV    720
YKALRSHILP PKHETEDGNI LQLANLPDLY KVFERC                              756
```

MLH1 (human) (SEQ ID NO:14)

```
cttggctctt ctggcgccaa aatgtcgttc gtggcagggg ttattcggcg gctggacgag     60
acagtggtga accgcatcgc ggcgggggaa gttatccagc ggccagctaa tgctatcaaa    120
gagatgattg agaactgttt agatgcaaaa tccacaagta ttcaagtgat tgttaaagag    180
ggaggcctga agttgattca gatccaagac aatggcaccg gatcaggaa agaagatctg    240
gatattgtat gtgaaaggtt cactactagt aaactgcagt cctttgagga tttagccagt    300
atttctacct atggctttcg aggtgaggct ttggccagca taagccatgt ggctcatgtt    360
actattacaa cgaaaacagc tgatggaaag tgtgcataca gagcaagtta ctcagatgga    420
aaactgaaag cccctcctaa accatgtgct ggcaatcaag gacccagat cacggtggag     480
gaccttttt acaacatagc cacgaggaga aaagctttaa aaaatccaag tgaagaatat    540
gggaaaattt tggaagttgt tgcaggtat tcagtacaca atgcaggcat agtttctca    600
gttaaaaaac aaggagagac agtagctgat gttaggacac tacccaatgc ctcaaccgtg    660
gacaatattc gctccatctt tggaaatgct gttagtcgag aactgataga aattggatgt    720
gaggataaaa ccctagcctt caaatgaat ggttacatat ccaatgcaaa ctactcagtg    780
aagaagtgca tcttcttact cttcatcaac catcgtctgg tagaatcaac ttccttgaga    840
aaagccatag aaacagtgta tgcagcctat ttgcccaaaa acacacaccc attcctgtac    900
ctcagtttag aaatcagtcc ccagaatgtg atgttaatg tgcaccccac aaagcatgaa    960
gttcacttcc tgcacgagga gagcatcctg agcgggtgc agcagcacat cgagagcaag   1020
ctcctgggct ccaattcctc caggatgtac ttcacccaga ctttgctacc aggacttgct   1080
ggcccctctg gggagatggt taaatccaca acaagtctga cctcgtcttc tacttctgga   1140
agtagtgata aggtctatgc ccaccagatg gttcgtacag attcccggga acagaagctt   1200
gatgcatttc tgcagcctct gagcaaaccc ctgtccagtc agccccaggc cattgtcaca   1260
gaggataaga cagatatttc tagtggcagg gctaggcagc aagatgagga gatgcttgaa   1320
ctcccagccc ctgctgaagt ggctgccaaa aatcagagct ggaggggga tacaacaaag   1380
gggacttcag aaatgtcaga agagagga cctacttcca gcaacccag aaagagacat   1440
cgggaagatt ctgatgtgga aatggtggaa gatgattccc gaaaggaaat gactgcagct   1500
tgtaccccc ggagaaggat cattaacctc actagtgttt tgagtctcca ggaagaaatt   1560
aatgagcagg gacatgaggt tctccgggag atgttgcata accactcctt cgtgggctgt   1620
gtgaatcctc agtgggcctt ggcacagcat caaaccaagt tataccttct caacaccacc   1680
aagcttagtg aagaactgtt ctaccagata tcatttatg attttgccaa ttttggtgtt   1740
ctcaggttat cggagccagc accgctcttt gaccttgcca tgcttgcctt agatagtcca   1800
```

```
                                     -continued
gagagtggct ggacagagga agatggtccc aaagaaggac ttgctgaata cattgttgag    1860
tttctgaaga agaaggctga gatgcttgca gactatttct ctttggaaat tgatgaggaa    1920
gggaacctga ttggattacc ccttctgatt gacaactatg tgcccctttt ggagggactg    1980
cctatcttca ttcttcgact agccactgag gtgaattggg acgaagaaaa ggaatgtttt    2040
gaaagcctca gtaaagaatg cgctatgttc tattccatcc ggaagcagta catatctgag    2100
gagtcgaccc tctcaggcca gcagagtgaa gtgcctggct ccattccaaa ctcctggaag    2160
tggactgtgg aacacattgt ctataaagcc ttgcgctcac acattctgcc tcctaaacat    2220
ttcacagaag atggaaatat cctgcagctt gctaacctgc ctgatctata caaagtcttt    2280
gagaggtgtt aaatatggtt atttatgcac tgtgggatgt gttcttcttt ctctgtattc    2340
cgatacaaag tgttgtatca aagtgtgata tacaaagtgt accaacataa gtgttggtag    2400
cacttaagac ttatacttgc cttctgatag tattcctttta tacacagtgg attgattata   2460
aataaataga tgtgtcttaa cata                                           2484 hPMS2-134 (human) (SEQ ID NO:15)

MERAESSSTE PAKAIKPIDR KSVHQICSGQ VVLSLSTAVK ELVENSLDAG ATNIDLKLKD     60

YGVDLIEVSD NGCGVEEENF EGLTLKHHTS KIQEFADLTQ VETFGFRGEA LSSLCALSDV   120

TISTCHASAK VGT                                                      133 hPMS2-134 (human cDNA) (SEQ ID NO:16)

cgaggcggat cgggtgttgc atccatggag cgagctgaga gctcgagtac agaacctgct    60
aaggccatca aacctattga tcggaagtca gtccatcaga tttgctctgg gcaggtggta   120
ctgagtctaa gcactgcggt aaaggagtta gtagaaaaca gtctggatgc tggtgccact   180
aatattgatc taaagcttaa ggactatgga gtggatctta ttgaagtttc agacaatgga   240 tgtgggtag aagaagaaaa cttcgaaggc ttaactctga aacatcacac atctaagatt    300
caagagtttg ccgacctaac tcaggttgaa acttttggct ttcggggga agctctgagc    360 tcactttgtg cactgagcga tgtcaccatt tctacctgcc acgcatcggc gaaggttgga   420
acttga                                                               426
```

For further information on the background of the invention the following references may be consulted, each of which is incorporated herein by reference in its entirety:

1. John, T. J. (2000) The final stages of the global eradication of polio. *New Engl. J. Med* 14:806–807.
2. Boyce, T. G. et al. (2000) Safety and immunogenicity of adjuvanted and unadjuvanted subunit influenza vaccines administered intranasally to healthy adults. *Vaccine* 19:217–226.
3. Hoshino, Y. and A. Z. Kapikian (2000) Rotavirus serotypes: classification and importance in epidemiology, immunity, and vaccine development. *J. Health Popul. Nutr.* 18:5–14.
4. Orenstein, W. A. et al. (2000) Measles eradication: is it in our future? *Am. J. Public Health* 90:1521–525.
5. Lechmann, M, and T. J. Liang (2000) Vaccine development for hepatitis C. *Semin. Liver Dis.* 20:211–226.
6. Ausiello, C. M. et al. (1999) Cell-mediated immune responses in four-year-old children after primary immunization with acellular pertussis vaccines. *Infect. Immun.* 67:4064–4071.
7. Brosstoff, S. (1995) The development and use of T cell receptor peptide vaccines. *Adv. Exp. Med. Biol.* 383:249–254.
8. Oaks, S. C., Jr. V. S. Mitchell, G. W. Pearson, and C. J. Carpenter (1991) MALARIA OBSTACLES AND OPPORTUNITIES, National Academy Press, p. 1, 1991.
9. Anders, R. F. "Vaccines against asexual blood stages of *Plasmodium falciparum*" NEW GENERATION VACCINES, $2^{nd}$ Ed., pp. 1035–1055, 1997.
10. McLeod, R. et al. (1995) Immunogenetics in the analysis of resistance to intracellular pathogens. *Curr. Opin. Immunol.* 7:539–552.
11. Corbel, M. J. (1996) Reasons for instability of bacterial vaccines. *Dev. Biol. Stand.* 87:113–124.
12. Kniskern, P. J. et al. (1994) Characterization and evaluation of a recombinant hepatitis B vaccine expressed in yeast defective for N-linked hyperglycosylation. *Vaccine* 12:1021–1025.
13. Kim, K. et al. (1994) Conformationally appropriate expression of the Toxoplasma antigen SAG1 (p30) in CHO cells. *Infect. Immun.* 62:203–209.
14. Baker, S. M. et al. (1995) Male defective in the DNA mismatch repair gene PMS2 exhibit abnormal chromosome synapsis in meiosis. *Cell* 82:309–319.
15. Bronner, C. E. et al. (1994) Mutation in the DNA mismatch repair gene homologue hMLH1 is associated with hereditary non-polyposis colon cancer. *Nature* 368:258–261.

16. de Wind N. et al. (1995) Inactivation of the mouse Msh2 gene results in mismatch repair deficiency, methylation tolerance, hyperrecombination, and predisposition to cancer. *Cell* 82:321–300.
17. Drummond, J. T. et al. (1995) Isolation of an hMSH2-p160 heterodimer that restores mismatch repair to tumor cells. *Science* 268:1909–1912.
18. Modrich, P. (1994) Mismatch repair, genetic stability, and cancer. *Science* 266:1959–1960.
19. Hoang, J. M. et al. (1997) BAT-26, an indicator of the replication error phenotype in colorectal cancers and cell lines. *Cancer Res.* 15:300–303.
20. Jiricny, J. and M. Nystrom-Lahti (2000) Mismatch repair defects in cancer. *Curr. Opin. Genet. Dev.* 10:157–161.
21. Nicolaides, N. C. et al. (1998) A naturally occurring hPMS2 mutation can confer a dominant negative mutator phenotype. *Mol. Cell. Biol.* 18:1635–1641.
22. Prolla, T. A. et al. (1994) MLH1, PMS1, and MSH2 interaction during the initiation of DNA mismatch repair in yeast. *Science* 264:1091–1093.
23. Strand, M. et al. (1993) Destabilization of tracts of simple repetitive DNA in yeast by mutations affecting DNA mismatch repair. *Nature* 365:274–276.
24. Su, S. S., R. S. Lahue, K. G. Au, and P. Modrich (1988) Mispair specificity of methyl directed DNA mismatch corrections in vitro. *J. Biol. Chem.* 263:6829–6835.
25. Parsons, R. et al. (1993) Hypermutability and mismatch repair deficiency in RER+tumor cells. *Cell* 75:1227–1236.
26. Papadopoulos, N. et al. (1993) Mutation of a mutL homolog is associated with hereditary colon cancer. *Science* 263:1625–1629.
27. Perucho, M. (1996) Cancer of the microsatellite mutator phenotype. *Biol. Chem.* 377:675–684.
28. Karran P. and R. Hampson (1996) Genomic instability and tolerance to alkylating agents. *Cancer. Surv.* 28:69–85.
29. Palombo, F. et al. (1994) Mismatch repair and cancer. *Nature* 36:417.
30. Eshleman J. R. and S. D. Markowitz (1996) Mismatch repair defects in human carcinogenesis. *Hum. Mol. Genet.* 5:1489–494.
31. Liu, T. et al. (2000) Microsatellite instability as a predictor of a mutation in a DNA mismatch repair gene in familial colorectal cancer. *Genes Chrom. Cancer* 27:17–25.
32. Devos et al. (1983) Molecular cloning of human interleukin-2 cDNA and its expression in *E. coli. Nucl. Acids Res.* 11:4307–4323.
33. Nicolaides, N. C., et al. (1995) Genomic organization of the human PMS2 gene family. *Genomics* 30:195–206
34. Papadopoulos, N. et al. (1994) Mutation of a mutL homolog in hereditary colon cancer. *Science* 263:1625–1629.
35. Papadopoulos, N., et al. (1995) Mutations of GTBP in genetically unstable cells. *Science* 268:1915–1917.
36. Nicolaides, N. C. et al. (1997) Interleukin 9: a candidate gene for asthma. *Proc. Natl. Acad. Sci. USA* 94:13175–13180.
37. Grasso, L. et al. (1998) Molecular analysis of human interleukin-9 receptor transcripts in peripheral blood mononuclear cells. Identification of a splice variant encoding for a nonfunctional cell surface receptor. *J Biol. Chem.* 273:24016–24024.
38. Sela, M. (2000) Structural components responsible for peptide antigenicity. *Appl. Biochem. Biotechnol.* 83:63–70.
39. Galio, L. et al. (1999) ATP hydrolysis-dependent formation of a dynamic ternary nucleoprotein complex with MutS and MutL. *Nucl. Acids Res.* 27:2325–2331.
40. Spampinato, C. and P. Modrich (2000) The MutL ATPase is required for mismatch repair. *J. Biol. Chem.* 275:9863–9869.

The above disclosure generally describes the present invention. A more complete understanding can be obtained by reference to the following specific examples which are provided herein for purposes of illustration only, and are not intended to limit the scope of the invention.

EXAMPLE 1

Stable Expression of Dominant Negative MMR Genes in Cells Results in Widespread Mutations of a Reporter Gene and its Encoded Polypeptide Expression of a dominant negative allele in an otherwise MMR proficient cell could render these host cells MMR deficient (Nicolaides, N. C. et al. (1998) *Mol. Cell. Biol.* 18:1635–1641). The creation of MMR deficient cells can lead to the generation of genetic alterations throughout the entire genome of a host organisms offspring, yielding a population of genetically altered offspring or siblings that may produce biochemicals with altered properties. This patent application teaches of the use of dominant negative MMR genes in antigen-producing cells, including but not limited to rodent, human, primate, yeast, insect, and prokaryotic cells producing proteins that may serve as therapeutic antigens for vaccination. The cell expression systems described above that are used to produce antigens are well known by those skilled in the art of vaccine therapeutics.

To demonstrate the ability to create MMR defective mammalian cells using dominant negative alleles of MMR genes, we first transfected a MMR proficient rodent cell line with an expression vector containing the human the previously published dominant negative PMS2 mutant referred herein as PMS134 (cell line referred to as TKPMS134), or with no insert (cell line referred to as TKvec). A fragment containing the PMS134 cDNA was cloned into the pEF expression vector which contains the constitutively active elongation factor promoter along with the neomycin resistance gene as selectable marker. The results showed that the PMS134 mutant could exert a robust dominant negative effect, resulting in biochemical and genetic manifestations of MMR deficiency. A brief description of the methods are provided below.

A hallmark of MMR deficiency is the generation of unstable microsatellite repeats in the genome of host cells. This phenotype is referred to as microsatellite instability (MI). MI consists of deletions and/or insertions within repetitive mono-, di- and/or tri nucleotide repetitive sequences throughout the entire genome of a host cell. Extensive genetic analysis eukaryotic cells have found that the only biochemical defect that is capable of producing MI is defective MMR. In light of this unique feature that defective MMR has on promoting MI, it is now used as a biochemical marker to survey for lack of MMR activity within host cells.

A method used to detect MMR deficiency in eukaryotic cells is to employ a reporter gene that has a polynucleotide repeat inserted within the coding region that disrupts its reading frame due to a frame shift. In the case where MMR is defective, the reporter gene will acquire random mutations (i.e. insertions and/or deletions) within the polynucelotide repeat yielding clones that contain a functional reporter gene. An example of the ability to alter desired genes via defective MMR comes from experiments using Syrian Hamster fibroblasts (TK) cells (described above), where a mammalian expression construct containing a defective β-galactosidase gene (referred to as pCAR-OF) was transfected into TKPMS134 or TKvect cells as described above. The pCAR-OF vector consists of a β-galactosidase gene containing a 29-basepair poly-CA tract inserted at the 5' end of its coding region, which causes the wild-type reading frame to shift out-of-frame. This chimeric gene is cloned into the pCEP4, which contains the constitutively cytomegalovirus (CMV) promoter upstream of the cloning site and also contains the hygromycin-resistance (HYG) gene that allows for selection of cells containing this vector. The pCAR-OF reporter cannot generate β-galactosidase activity unless a frame-restoring mutation (i.e., insertion or deletion) arises following transfection into a host. Another reporter vector called pCAR-IF contains a β-galactosidase in which a 27-bp poly-CA repeat was cloned into the same site as the pCAR-OF gene, but it is biologically active because the removal of a single repeat restores the open reading frame and produces a functional chimeric β-galactosidase polypeptide (not shown). The pCAR vectors also contain the neomycin resistance gene as selectable marker. In these proof-of-concept studies, TKPMS134 and TKvect cells were transfected with the pCAR-OF reporter vector and selected for 17 days in neomycin plus hygromycin selection medium. After the 17$^{th}$ day, resistant colonies were stained for β-galactosidase production to determine the number of clones containing a genetically altered β-galactosidase gene. All conditions produced a relatively equal number of neomycin/hygromycin resistant cells, however, only the cells expressing the PMS134 dominant negative allele (TKPMS134) contained a subset of clones that were positive for β-galactosidase activity (Table 1). This result was also observed using a similar experimental strategy with a MMR proficient human cell line (data not shown). Table 1 shows the data from these experiments, where cell colonies were stained in situ for β-galactosidase activity and scored for activity. Cells were scored positive if the colonies turned blue in the presence of X-gal substrate and scored negative if colonies remained white. Analysis of triplicate experiments showed a significant increase in the number of β-galactosidase positive cells in the TKPMS134 cultures, while no β-galactosidase cells were seen in the control TKvect cells.

TABLE 1

Number of TKPMS134 and TKvect cells containing functional β-galactosidase gene as a result of MMR deficiency.

| Cells | White Colonies | Blue Colonies | % Clones with altered B-gal |
|---|---|---|---|
| TKvect | 65 +/−9 | 0 | 0/65 = 0% |
| TKPMS134 | 40 +/−12 | 28 +/−4 | 28/68 = 41% |

Table 1. β-galactosidase expression of HBvec, HBPMS2 and HB134 cells transfected with pCAR-OF reporter vectors. Cells were transfected with the pCAR-OF β-galactosidase reporter plasmid. Transfected cells were selected in hygromycin and G418, expanded and stained with X-gal solution to measure for β-galactosidase activity (blue colored cells). 3 plates each were analyzed by microscopy. The results below represent the mean +/−standard deviation of these experiments.

TKPMS134/pCAR-OF clones that were pooled and expanded also showed a number of cells that contained a functional β-galactosidase gene. No β-galactosidase positive cells were observed in TKvect cells transfected with the pCAR-OF vector. These data are shown in FIG. 1 where the dark staining in panel B represent β-galactosidase positive cells present in the TKPMS134/pCAR-OF cultures while none are found in the TKvect cells grown under similar conditions (panel A). These data demonstrate the ability of dominant negative alleles of MMR genes to generate in vivo gene alterations, which allows for the rapid screening of clones with altered polypeptides exhibiting new biochemical features.

To confirm that alterations within the nucleotide sequences of the β-galactosidase gene was indeed responsible for the in vivo β-galactosidase activity present in TKPMS134 clones, RNA was isolated from TKPMS134/pCAR-OF and TKvect/pCAR-OF and the β-galactosidase mRNA primary structure was examined by reverse transcriptase polymerase chain reaction (RT-PCR) amplification and sequencing. Sequence analysis of β-galactosidase message from TKvect cells found no structural alterations in the input gene sequence. Analysis of the β-galactosidase message from TKPMS134 cells found several changes within the coding sequences of the gene. These sequence alterations included insertion and deletions of the poly-CA tract in the amino terminus as expected. Other alterations included insertions of sequences outside of the poly-CA repeat as well as a series of single base alterations (transversions and transitions) contained throughout the length of the gene.

In Situ X-gal Staining

For in situ analysis, 100,000 cells are harvested and fixed in 1% gluteraldehyde, washed in phosphate buffered saline solution and incubated in 1 ml of X-gal substrate solution [0.15 M NaCl, 1 mM MgCl$_2$, 3.3 mM K$_4$Fe(CN)$_6$, 3.3 mM K$_3$Fe(CN)$_6$, 0.2% X-Gal] in 24 well plates for 2 hours at 37° C. Reactions are stopped in 500 mM sodium bicarbonate solution and transferred to microscope slides for analysis. Three plates each are counted for blue (β-galactosidase positive cells) or white (β-galactosidase negative cells) to assess for MMR inactivation. Table 1 shows the results from these studies.

EXAMPLE 2

Generation of an Expression Cassette for Screening of Structurally Altered Polypeptides in MMR Defective Cells In order to produce recombinant proteins for screening of highly antigenic polypeptides, a fusion gene cassette was engineered that encodes for a secreted polypeptide containing a six polyhistidine domain at the C-terminus, which is useful for purification. This gene cassette is referred to as sec-hist. This gene was constructed by PCR using DNA from the pUC18 plasmid as template. The sense primers contained nucleotide sequences corresponding to the leader sequence of human interleukin-2 (ref 32), which has been found to produce robust amounts of secreted polypeptides from TK cells (personal observation). This domain was introduced at the 5' end of the pUC18 polylinker. Antisense primers containing nucleotide sequences encoding for 6 histidines were used to position these residues at the 3' end of the pUC18 polylinker. The nucleotide sequence of these primers are listed below.

SENSE Primer:

5'aagcttccatgtacaggatgcaactcctgtcttgcattgcactaagtcttgcacttgtcacaaacagtgcaCAAAAGCTGGA
GCTC-3' (SEQ ID NO:1)

The italic sequence represents a HindIII site for subcloning. The underlined sequence represents leader sequence from the human IL-2. Sequence in capital letters represents sequence from the start of the polylinker region of pUC 18.
ANTISENSE Primer:

5'ccggatccctactagtggtgatggtgatggtgGCTTGATATCGAATTCCTG-3' (SEQ ID NO:2)

The italic sequence represents a HindIII site for subcloning. The underlined sequence represents 6 codons encoding for histidine residues followed by 2 termination codons. Sequence in capital letters represents sequence to the 3' end of the pUC18 polylinker.

Amplified products were obtained using buffer conditions as previously described. Amplification reactions were carried out at 94° C. for 30 sec, 52° C. for 2 min, and 72° C. for min for 25 cycles. Products were run on 1% agarose gels containing ethidium bromide, and products of the expected molecular weight were excised and purified by Gene Clean (Bio101). Products were then cloned into T-tailed vectors (InVitrogen) as suggested by the manufacturer. Recombinant clones were analyzed by restriction analysis and by DNA sequencing. Several clones contained fragments with the expected genomic sequence. The parental clone is referred to as TAsec-hist.

A schematic diagram of the sec-hist fusion protein is shown in FIG. 3A In order to generate TK cells that secrete the sec-hist polypeptide, the TAsec-hist plasmid is digested with HindIII to release the sec-hist insert. The insert was cloned into the unique HindIII site of the pCEP4 mammalian expression vector, which also contains the Hygromycin resistance gene as selectable marker. Recombinant clones were analyzed by restriction digest and sequencing to assure the authenticity of the construct.

Inserts can now be designed via PCR or direct cloning using the restricition sites contained within the polylinker (see FIG. 3B).

Recombinant pCEPsec-hist plasmid will then be transfected into TK cells as previously described using cationic lipids. Cells will be cotransfected along with the pEFPMS134, which is a mammalian expression vector containing the PMS134 dominant negative MMR gene allele under control of the constitutive elongation factor (EF) promoter. This vector contains the neomycin resistance gene and allows for double selection of TK cells for both the sec-hist and pEFPMS134 vectors. TK cells will also be cotransfected with the sec-hist and pEF empty vector as a control.

Cells are co-selected for 14 days in 0.6 mg/ml G418 and 0.8 mg/ml hygromycin B (these concentrations have been previously determined for double transfection of TK cells). After 14 days, macroscopic colonies will be isolated and subcloned into 24 well dishes (Nunc) as 1 ml cultures. Clones will then be analyzed for secreted sec-hist protein using both ELISA and western blot analysis of conditioned supernatants from sec-hist/pEFPMS134, sec-hist/pEFempty vector, and parental TK cells. A monoclonal anti-HIS antibody (Santa Cruz), which has been successfully used for other western and ELISA studies, will be used for both assays. Analysis of PMS134 expression will be determined by western blot using a PMS2-specific polyclonal antibody (Morphotek, personal communication).

ELISA will be performed on conditioned medium (CM) from TK cells transfected with pCEP4sec-hist to screen for high producers of the sec-hist polypeptide. ELISAs are carried out as follows. Two hundred microliter aliquots of conditioned medium are taken from pCEP4sec-hist transfected and control cells. Aliquots are placed into 1.5 ml eppendorf tubes and centrifuged at 14,000×g for 3 minutes to pellet cell debris. Supernates are then collected and 50 μls are placed into triplicate wells of a 96-well polystyrene microtiter plate (Nunc). Plates are incubated at room temperature for 4 hours, washed twice with 200 μls of 1×Phosphate Buffered Saline (PBS) solution, pH 7.0 (Life Technologies), and blocked with 100 μls of 5% milk in 1×PBS for 1 hour. Plates are then incubated with a monoclonal anti-HIS antibody (diluted 1:1000 in 1×PBS) (Santa Cruz) for 2 hours at room temperature and then washed twice with 200 μls of 1×PBS, and probed with an anti-mouse-horse radish peroxidase (HRP) conjugated secondary antibody diluted 1:3000 in PBS. Plates are then incubated at room temperature for 1 hour, washed three times with 200 μls of 1×PBS and incubated with TMB substrate (BioRad) for 15–30 minutes. After incubation is completed, reactions are stopped using 0.1N $H_2SO_4$ and plates are read using a BioRad microplate reader at 415 nm. Clones are determined to be positive for secreted sec-hist if expected cells are found to produce a significant signal over control cells. Conditioned medium from positive cultures will then be analyzed by western blot using the anti-HIS antibody as probe to confirm ELISA data.

Western blot analysis will be carried out as follows. Briefly, 50 μls of CM or 50,000 cells from each culture is directly lysed in 2×lysis buffer (60 mM Tris, pH 6.8, 2% SDS, 10% glycerol, 0.1 M 2-mercaptoethanol, 0.001% bromophenol blue) and samples are boiled for 5 minutes. Lysate proteins are separated by electrophoresis on 4–20% Tris glycine gels (Novex) and then electroblotted onto Immobilon-P (Millipore) in 48 mM Tris base, 40 mM glycine, 0.0375% SDS, 20% methanol and blocked overnight at 4° C. in Tris-buffered saline plus 0.05% Tween-20 and 5% condensed milk. Filters are then probed with an antibody generated against the PMS134 or the polyHIS tag (Santa Cruz), followed by a secondary HRP-conjugated antibody. After incubation with the secondary antibody, blots are developed using chemiluminescence (Pierce) and exposed to film to determine PMS134 and sec-hist expression. Clones exhibiting expression of both genes will then be used in experiments described above.

A potential technical problem may exist in expressing the sec-hist protein due to toxicity that it may have on the growth of TK cells. If the production of no or low amounts of sec-hist polypeptide is found to occur in the above analysis, a HindIII sec-hist fragment from the TAsec-hist plasmid will be subcloned into the unique HindIII site of the pIND/V5 steroid inducible vector (Invitrogen). This vector has been found to produce robust protein expression in TK cells upon in steroid induction. This application teaches the use of employing an inducible vector containing the sec-hist expression cassette to express polypeptides in TK cells that may be toxic under constitutively expressed conditions. Cells that are found to co-express the PMS134 and the sec-hist genes or the control cell expressing the pEF empty vector and the sec-hist gene are cultured under high growth conditions in media containing neomycin, hygromycin and vitamins, which has been shown to increase the doubling time of TK cells and enhance the genetic alteration of β-galactosidase reporter plasmids in vivo (data not shown). Briefly, cells are grown in vitamin enriched medium for 20 doublings (~17 days), a time at which it has been found that 20–40% of clones contain sequence alterations within a particular genetic locus. After selection, cells will be subcloned in 96-well microtiter plates by limiting dilutions. Clones will be grown for 5 days in the presence of neomycin/hygromycin-free medium containing heat inactivated serum to remove complement for in vitro antigenic assays that will be performed using murine lymphocytes as described in section below.

The sec-hist expression vector cassette can also be transfected into cell lines that are "naturally" defective for MMR such as the human cell lines derived from colon cancer tumors such as but not limited to HCT116 and DLD-1. The vector can be in the constitutive backbone pCEP4 or under control of the steroid-inducible vectors pIND or pMAM.

The techniques described above teach us the use of producing structurally altered antigens from mammalian cells to ensure proper folding or post-translation modifications of the polypeptide. This approach gives an advantage over others that employ the use of prokaryotic, yeast or baculovirus produced antigens that have been found to produce weak antigenic responses due to misfolding or improper post-translational modifications.

EXAMPLE 3

Screening Strategy to Identify Cell Clones Producing Highly Antigenic Polypeptides In order to identify antigenic polypeptides produced by TKPMS134 cell clones, the following in vitro assays will be performed.

First, the lymphocyte stimulatory activity of sec-hist polypeptides will be measured by adding CM of TKsec-hist cells with or without the PMS134 to lymphocytes derived from naive or whole antigen exposed Balb/C mice. Briefly, 2 mice will be infected with whole antigen in the presence of Freund's Complete Adjuvant by subcutaneous injection in the tail with a 100-μl 1/1 mixture of complete Freund's adjuvant (CFA) (Difco). Two subcutaneous boosts will be performed with the same quantity of antigen, mixed 1/1 with incomplete Freund's adjuvant (Difco), after 2 and 4 weeks. Two control mice will receive adjuvant alone. Mice are sacrificed 5 days after the second boost (at day 33). Peripheral blood mononuclear cells (PBMCs) from whole blood and splenocytes from spleens of will be harvested following the previously described procedures (Nicolaides, N. C. et al. (1997) *Proc. Natl. Acad. Sci. USA* 94:13175–13180). For splenocyte assays, whole spleens are pressed through sterile wire mesh into RPMI medium (Life Technology). Next, cells are washed twice in RPMI and incubated for 10 minutes in RBC lysis buffer. Cells are then washed again and resuspended at $1 \times 10^5$ cells/ml in RPMI-1640 medium plus 10% heat inactivated fetal bovine serum. One hundred microliters of cells are aliquoted into twenty 96-well titer flat bottom plates.

For PBMC isolation, whole blood is isolated by eye puncture and collected into vacutainer tubes containing EDTA. An equal volume of PBS ($Mg^{2+}/Ca^{2+}$-free) is added to whole blood. PBMCs are isolated by centrifugation over Ficoll-Paque gradients (Pharmacia Biotech 17-1440-02). Purified cells are seeded at $1 \times 10^5$ cells/ml in RPMI 1640 containing 10% heat-inactivated fetal bovine serum (Life Technologies, Inc.) and 100 μls are plated in 96 well flat bottom microtiter plates and incubated at 37° C. in 5% $CO_2$.

To measure for T-cell activation, PBMCs and splenocytes from primed and non-primed mice are incubated with 10% conditioned medium (CM) from TKsec-hist cells with or without the PMS134 gene. 5 μ/ml of concavalinA (ConA) is used as a positive control for splenocyte culture assays, while 5 μ/ml phorbol 12-myristate 13-acetate and 1 μg/ml phytohemagglutinin (Sigma) are used as a positive control for PBMC cultures. CM from parental TK cells grown in the presence of RPMI with 10% heat inactivated medium will be used as negative control. Previous studies using CM from TK cells have found no stimulatory activity to be produced on PBMCs or splenocytes (N. Nicolaides, personal observation). Cultures are incubated at 37° C. in 5% $CO_2$ for 6 days and scored for antigenic activity as determined by proliferation assay. Proliferation is assayed using a modified protocol of the acid phosphatase assay as described (Grasso, L. et al. (1998) *J. Biol. Chem.* 273:24016–24024). Briefly, 50 μls of a buffer containing 0.1 M sodium acetate (pH 5.5), 0.1 % Triton X-100, and 10 mM p-nitrophenyl phosphate (Sigma 104 phosphatase substrate) is added directly to each well containing 0.2 ml of growth medium and incubated for 1.5 h at room temperature. Reactions are terminated by the addition of 0.05 N sodium hydroxide and quantified by absorbance at 410 nm using a BioRad plate reader. Data is represented as a stimulation index (SI), which is the proliferation of experimental data points divided by the mean of 10 aliquots of CM from TK parental cells. All experiments will be performed in at least triplicate.

It is expected that several TKsec-hist clones co-expressing the PMS134 protein will be found to have an enhanced antigenicity on PBMCs and/or splenocytes due to conformational changes that will occur within the coding region of the target antigen. These changes may form secondary domains that serve as T and/or B cell epitopes and in turn are responsible for stimulating their respective activation. Clones that reproducibly produce enhanced antigenic activation will be sequenced to confirm and identify that a structural alteration(s) has indeed occurred within the coding region of the gene. Sequence data may also shed additional light into the importance of critical domains within this candidate vaccine polypeptide for additional rounds of alteration that may lead to the creation of a super-antigen that may serve as a potent vaccine.

Sequence analysis of clones will be performed as follows. First positive clones will be expanded from 96-well plates to 24-well plates. Confluent wells will be expanded and cells will be harvested for RNA extraction. RNA extraction and reverse transcription will be carried out using the Trizol method as previously described (Nicolaides, N. C. et al. (1997) *Proc. Natl. Acad. Sci. USA* 94:13175–13180; Grasso, L. et al. (1998) *J. Biol. Chem.* 273:24016–24024). Reverse transcription will be carried out using Superscript II (Life Technology) as previously described (Nicolaides, N. C. et al. (1998) *Mol. Cell. Biol.* 18:1635–1641). cDNAs will be amplified to isolate the sec-hist transcript using the sense primer: 5'-catgtacaggatgcaactcctg-3' (SEQ ID NO:3), which is located at the IL-2 leader sequence site (see FIG. 3), and the antisense primer: 5'-tactagtggtgatggtgatggtg-3' (SEQ ID NO:4), which is located at the C-terminal polyhis site. Amplification is carried out at 94° C. for 30 sec, 52° C. for 2 min, 72° C. for 2 min for 30 cycles. Reactions are analyzed on agarose gels. If products of the expected molecular weight are generated then samples will be cleaned using the QIAquick PCR template kit (Qiagen) to remove PCR amplimers and sequenced using the following primers that cover the entire coding region of the sec-hist gene. Clones are then sequenced using primers specific to the gene encoding the antigen.

Clones producing genetically altered sec-hist polypeptides will then be expanded into T-75 flasks to a density that will enable for the sufficient production of secreted sec-hist polypeptide in the CM. Conditioned medium containing the sec-hist polypeptide is then collected, and centrifuged at 3,500×g for 10 minutes to remove cellular debris. CM is then loaded onto a 10 ml- HiTrap Nickel column following the manufacturer's protocol (Pharmacia). After absorption and washing, the column is treated with 200 mM imidazole to elute the fusion protein. Recovered polypeptides are then analyzed by SDS-PAGE using 4–12% NuPAGE gels (Novex) and silver stained following the manufacturer's protocol (Novex). Due to the random nature of defective MMR, the possibility exists that sec-hist alleles may be generated by clones producing enhanced antigenic polypeptides, which contain a nonsense or frame-shift mutation, therefore forming polypeptides lacking a polyHIS C-terminus. If a nonsense or frameshift mutation does occur in clones producing polypeptides with increased antigenicity, then the new allele is reengineered via PCR to contain a polyHIS tag at the C-terminus, and this new fusion protein will be rescreened as above.

Purified polypeptides will be rescreened at a final concentration of 10 μg/ml in the in vitro assays described above to confirm that the antigenic activity is indeed coming from the sec-hist protein. TK cells producing altered antigens with enhanced activity on both PBMCs and splenocytes will then be tested along with the non-altered sec-hist protein in vivo in Balb/C mice for the ability to illicit an immune response in the absence of adjuvant. A schematic diagram outlining the screening procedure is given in FIG. 4.

EXAMPLE 4

Screening Strategy to Identify Cell Clones Producing Highly Immunogenic Antigens To test the immunogenic potential that the altered polypeptides identified from EXAMPLE 3 have in vivo, Balb/C mice will be injected with the 6 most antigenic polypeptides and the wild type sec-hist polypeptide produced from TKEFempty/sec-hist cells in the absence of adjuvant. Briefly, mice will be immunized with 30 μgs of purified sec-hist protein in sterile phosphate buffered saline (PBS) without adjuvant by subcutaneous injection in the tail. One group of mice will receive a 100 μls of a mixture of polypeptides diluted 1/1 in complete Freund's adjuvant (CFA) (Difco) as a positive control. Two subcutaneous boosts will be performed with the same quantity of antigen, and the mouse receiving the polypeptide mixture with adjuvant will be boosted with a 1/1 mixture with incomplete Freund's adjuvant (Difco), at 2 and 4 weeks after the initial injection. Mice will be bled 5 and 15 days after the second boost (at day 33) to measure for antigen titers. Control mice will receive PBS alone. Before the start of immunization, a prebleed will be obtained from each mouse.

Immune responses will be measured by screening for whole Ig and sec-hist specific antibody titers by ELISA following the protocol described above. For antigen specific antisera titers, 96-well plates will be coated with a 50 uls of a solution containing 5 μg/ml each antigen used for vaccination in PBS. Plates will then be probed with serial dilutions of prebleeds, 5 day and 15 day bleeds. Detection of antibodies will be done using a sheep anti-mouse-HRP conjugated secondary antibody followed by incubation with TMB substrate as described above.

Success of the strategy proposed in this program will be demonstrated with the generation of antisera from mice immunized with altered sec-hist protein that is able to cross react with the native sec-hist protein. If no titers are found in the samples without adjuvant, mice will be administrated antigen in complete Freund's Adjuvant and titers analyzed 14 days later, followed by immunization in Incomplete Freund's at day 17 if no titers are found and analyzed at day 31.

A potential problem that may occur with the outlined strategy is that antibody titers may be generated against the sec-polyhistidine fusion domain. To determine if antisera is able to identify authentic sec-his polypeptides, the antigen lacking the polyhistidine domain will be generated by in vitro transcription-translation (TNT) in the presence of radiolabelled methionine. A template containing the sec-hist polypeptide will also be made and the encoded protein used as a control. Templates for the TNT reactions will be generated by PCR as described (Nicolaides, N. C. et al. (1998) *Mol. Cell. Biol.* 18:1635–1641). Briefly, the TAsec-hist plasmid will be used as template to amplify gene segments that encode for the untqagged antigen or the sec-hist tagged protein.

Translated polypeptides are first analyzed by SDS-PAGE gel electrophoresis and autoradiography to ensure that the polypeptide with the expected molecular weight are synthesized. Proteins are then immunoprecipitated using antiserum from vaccinated mice to determine if these antibodies recognize authentic antigen sequences. Briefly, immunoprecipitations are performed on in vitro-translated proteins by mixing the translation reaction mixtures with 100 μls of mouse antiserum or 1 μg of a HIS-specific monoclonal antibody (MAB) (Santa Cruz) in 400 μls of EBC buffer (50 mM Tris [pH 7.5], 0.1 M NaCl, 0.5% Nonidet P-40). After incubation for 1 h at 4° C., protein A-Sepharose (Sigma) is added to a final concentration of 10% and the reaction mixtures are incubated at 4° C. for 1 h. Proteins bound to protein A are washed five times in EBC and separated by electrophoresis on 4–20% Tris-glycine gradient gels, which are then dried and autoradiographed.

If antisera are able to react with authentic sequences lacking HIS residues, the data from these studies will be continued in further preclinical animal studies.

Discussion

The initial steps of MMR are dependent on two protein complexes, called MutSα and MutLα. The use of dominant negative MMR alleles are able to perturb the formation of these complexes with downstream biochemicals involved in the excision and polymerization of nucleotides comprising the "corrected" nucleotides. Examples from this application show the ability of a truncated MMR allele (PMS134 is capable of blocking MMR resulting in a hypermutable cell line that gains genetic alterations throughout its entire genome per cell division. Once a cell line is produced that contains genetic alterations within genes encoding for an antigen, it is desirable to restore the genomic integrity of the cell host. This can be achieved by the use of inducible vectors whereby dominant negative MMR genes are cloned into such vectors, introduced into antigen-producing cells and the cells are cultured in the presence of inducer molecules and/or conditions. Inducible vectors include but are not limited to chemical regulated promoters such as the steroid inducible MMTV, tetracycline regulated promoters, temperature sensitive MMR gene alleles, and temperature sensitive promoters.

The results described above lead to several conclusions. First, expression of PMS134 results in an increase in microsattelite instability in TK cells. That this elevated microsattelite instability is due to MMR deficiency was proven by evaluation of extracts from stably transduced cells and stability of a tract contained within the pCAR-OF vector. The expression of PMS134 results in a polar defect in MMR, which was only observed using heteroduplexes designed to test repair from the 5' direction (no significant defect in repair from the 3' direction was observed in the same extracts). Interestingly, cells deficient in hMLH1 also have a polar defect in MMR, but in this case preferentially affecting repair from the 3' direction. It is known from previous studies in both prokaryotes and eukaryotes that the separate enzymatic components mediate repair from the two different directions. These results strongly suggest a model in which 5' repair is primarily dependent on hPMS2 while 3' repair is primarily dependent on HMLH1. It is easy to envision how the dimeric complex between PMS2 and MLH1 might set up this directionality. The combined results also demonstrate that a defect in directional MMR is sufficient to produce a MMR defective phenotype and suggests that any MMR gene allele is useful to produce genetically altered TK cells, or a cell line that is producing antigenic gene products. Moreover, the use of such MMR alleles will be useful for generating genetically altered polypeptides with altered structures as effective vaccine agents.

This application also teaches us that ANY method used to block MMR can be performed to generate hypermutablility in an antigen-producing cell that can lead to genetically altered proteins with enhanced biochemical features such as but not limited to increased antigenicity, increased immunogenicity, and enhanced pharmacokinetic profiles.

The blockade of MMR in such cells can be through the use of dominant negative MMR gene alleles from any species including bacteria, yeast, protozoa, insects, rodents, primates, mammalian cells, and man. Blockade of MMR can also be generated through the use of antisense RNA or deoxynucleotides directed to any of the genes involved in the MMR biochemical pathway. Blockade of MMR can be through the use of polypeptides that interfere with subunits of the MMR complex including but not limited to antibodies. Finally, the blockade of MMR may be through the use of chemicals such as but not limited to nonhydrolyzable ATP analogs, which have been shown to block MMR (Galio, L. et al. (1999) *Nucl. Acids Res.* 27:2325–2331; Spampinato, C. and P. Modrich (2000) *J. Biol. Chem.* 275:9863–9869).

We claim:

1. A method for making a therapeutically hypermutated immunogen, comprising introducing into a cell that expresses a gene encoding a preselected immunogen in vitro a polynucleotide comprising a dominant negative allele of a mismatch repair gene, wherein said dominant negative allele is a truncation mutant of a PMS2, and selecting cells that comprise a mutation in said gene encoding said preselected immunogen.

2. The method of claim 1 wherein the PMS2 mismatch repair gene is human PMS2.

3. The method of claim 2 wherein the allele comprises a truncation mutation at codon 134.

4. The method of claim 3 wherein the truncation mutation is a thymidine at nucleotide 424 of wild-type PMS2.

5. A homogeneous composition of selected, cultured, hypermutable cells which comprise a therapeutically preselected immunogen and a dominant negative allele of a mismatch repair gene, wherein said dominant negative allele is a truncation mutant of a PMS2, wherein said hypermutable cells are selected based on a determination that said preselected immunogen is encoded by a polynucleotide that comprises a mutation as compared to the polynucleotide of a parental cell prior to introduction of said dominant negative allele of a PMS2 mismatch repair gene.

6. The homogeneous composition of cultured, hypermutable cells of claim 5 wherein the mismatch repair gene is human PMS2.

7. The homogeneous composition of cultured, hypermutable cells of claim 5 wherein the cells express a protein consisting of the first 133 amino acids of hPMS2.

8. The method of claim 1 wherein said introduction of said polynucleotide is in the presence of at least one DNA mutagen.

9. The method of claim 1 further comprising restoring genetic stability of the selected cells.

10. A homogeneous culture of selected cells produced by the method of claim 9, wherein the cells are selected based on a determination that the polynucleotide encoding said preselected immunogen comprises a mutation as compared to the polynucleotide of a parental cell prior to introduction of said dominant negative allele of a PMS2 mismatch repair gene, and wherein said dominant negative allele of said polynucleotide is inactivated.

* * * * *

UNITED STATES PATENT AND TRADEMARK OFFICE
CERTIFICATE OF CORRECTION

PATENT NO. : 6,737,268 B1
APPLICATION NO. : 09/712691
DATED : May 18, 2004
INVENTOR(S) : Nicholas C. Nicolaides et al.

It is certified that error appears in the above-identified patent and that said Letters Patent is hereby corrected as shown below:

Title Page,
Item (56), References Cited, OTHER PUBLICATIONS:
"Vora, K.A., et al.," reference, delete "celll" and insert -- cell --.
"Ma et al.," reference, delete "Experssion" and insert -- Expression --.
"Nicolaides, N.C., et al.," reference, delete "*Moecular*" and insert -- *Molecular* --.
"Peinado, M.A., et al.," reference, delete "lossesand" and insert -- losses and --.

Column 4,
Line 25, delete "HindIll" and insert -- HindIII --.
Line 33, delete "XbaI-SpeI-BamHI-SmaI-PstI-EcoRI." and insert
-- XbaI-SpeI-BamHI-SmaI-PstI-EcoRI. --.
Line 37, delete "naive" and insert -- naïve --.

Column 6,
Line 22, delete "alleies" and insert -- alleles --.

Column 27,
Line 48, after "206" insert -- . --.

Column 29,
Table 1, delete "% Clones with aitered B-gal" and insert -- % Clones with altered B-gal --.

Column 31,
Line 35, delete "FIG. 3A In" and insert -- FIG. 3A.  In --.
Line 44, delete "restricition" and insert -- restriction --.

Column 32,
Line 45, delete "2Xylsis" and insert -- 2X lysis --.

Column 33,
Line 47, delete "naive" and insert -- naïve --.

UNITED STATES PATENT AND TRADEMARK OFFICE
CERTIFICATE OF CORRECTION

PATENT NO. : 6,737,268 B1
APPLICATION NO. : 09/712691
DATED : May 18, 2004
INVENTOR(S) : Nicholas C. Nicolaides et al.

It is certified that error appears in the above-identified patent and that said Letters Patent is hereby corrected as shown below:

Column 34,
Line 13, delete "5 μ/ml" and insert -- 5 μg/ml --.
Line 15, delete "5 μ/ml" and insert -- 5 μg/ml --.

Column 36,
Line 2, delete "50 uls" and insert -- 50 μls --.
Line 54, delete "MutScα" and insert -- MutSα --.

Column 37,
Line 24, delete "HMLH1." and insert -- hMLH1. --.

Signed and Sealed this

Twenty-ninth Day of January, 2008

JON W. DUDAS
*Director of the United States Patent and Trademark Office*